United States Patent
Vilermo et al.

(10) Patent No.: US 9,588,498 B2
(45) Date of Patent: Mar. 7, 2017

(54) METHOD AND APPARATUS FOR PROVIDING AN INTELLIGENT ALARM NOTIFICATION

(71) Applicant: Nokia Corporation, Espoo (FI)

(72) Inventors: Miikka Tapani Vilermo, Siuro (FI); Jussi Artturi Leppanen, Tampere (FI); Antti Johannes Eronen, Tampere (FI); Arto Juhani Lehtiniemi, Lempaala (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 30 days.

(21) Appl. No.: 14/585,972

(22) Filed: Dec. 30, 2014

(65) Prior Publication Data
US 2016/0187856 A1 Jun. 30, 2016

(51) Int. Cl.
*G08B 23/00* (2006.01)
*G04G 21/02* (2010.01)
(Continued)

(52) U.S. Cl.
CPC ......... *G04G 21/025* (2013.01); *A61B 5/0816* (2013.01); *A61B 5/4812* (2013.01);
(Continued)

(58) Field of Classification Search
None
See application file for complete search history.

(56) References Cited

U.S. PATENT DOCUMENTS 7,656,287 B2 2/2010 Albert et al.
8,140,143 B2 3/2012 Picard et al.
(Continued)

FOREIGN PATENT DOCUMENTS

DE 4209336 A1 9/1993
JP 09292479 A 11/1997
WO 2011/117903 A2 9/2011

OTHER PUBLICATIONS

MedGadget, "Resmed S+ Non-contact Sleep Monitoring System, an Advanced Tracker for Your Zs (video)", posted Oct. 7, 2014, retrieved on Oct. 31, 2014 from http://www.medgadget.com/2014/10/resmed-s-non-contact-sleep-monitoring-system-an-advanced-tracker-for-your-zs-video.html, pp. 1-4.
(Continued)

*Primary Examiner* — Brian Zimmerman
*Assistant Examiner* — Kevin Lau
(74) *Attorney, Agent, or Firm* — Ditthavong & Steiner, P.C.

(57) ABSTRACT

An approach is provided for providing alarm notification to the intended user while minimizing disturbance to the nearby users. The approach involves determining sensor information associated with at least one first user and at least one second user collected while the at least one first user and the at least one second user are asleep. The approach also involves processing and/or facilitating a processing of the sensor information to determine sleep characteristic information for the at least one first user, the at least one second user, or a combination thereof. The approach further involves determining one or more alarm notification parameters for one or more alarm notifications based, at least in part, on the sleep characteristic information to direct the one or more alarm notifications to the at least one first user while minimizing a disturbance of the at least one second user.

20 Claims, 18 Drawing Sheets

(51) Int. Cl.
*A61B 5/08* (2006.01)
*G04G 13/02* (2006.01)
*A61B 5/00* (2006.01)
*A61B 7/00* (2006.01)

(52) U.S. Cl.
CPC .......... *A61B 5/4815* (2013.01); *A61B 5/4818* (2013.01); *A61B 5/6898* (2013.01); *A61B 5/7264* (2013.01); *A61B 5/746* (2013.01); *A61B 5/7415* (2013.01); *G04G 13/023* (2013.01); *G04G 13/026* (2013.01); *A61B 5/0022* (2013.01); *A61B 5/743* (2013.01); *A61B 5/749* (2013.01); *A61B 7/003* (2013.01)

(56) References Cited

U.S. PATENT DOCUMENTS

| | | | |
|---|---|---|---|
| 8,493,220 B2 | 7/2013 | Virtanen et al. | |
| 8,781,568 B2 | 7/2014 | Dugan et al. | |
| 2007/0249952 A1* | 10/2007 | Rubin | A61B 5/0476 600/544 |
| 2011/0066205 A1* | 3/2011 | Crompvoets | A61B 5/02405 607/17 |
| 2011/0096637 A1* | 4/2011 | Chiang | G04C 19/02 368/256 |
| 2011/0267196 A1 | 11/2011 | Hu et al. | |
| 2014/0276227 A1* | 9/2014 | Perez | A61B 5/4818 600/586 |
| 2014/0371635 A1* | 12/2014 | Shinar | A61B 5/6891 600/595 |
| 2015/0173671 A1* | 6/2015 | Paalasmaa | A61B 5/0022 600/301 |
| 2015/0346845 A1* | 12/2015 | Di Censo | G06F 3/167 707/766 |
| 2016/0015315 A1* | 1/2016 | Auphan | A61B 5/4815 600/301 |

OTHER PUBLICATIONS

Youtube, "Directional Alarm Clock", posted Oct. 15, 2008, retrieved on Mar. 30, 2015 from https://www.youtube.com/watch?v=92rYLOTazIU, 1 page.

Sleep Cycle, "Sleep Cycle alarm clock", retrieved on Mar. 30, 2015 from http://www.sleepcycle.com/, 1 page.

* cited by examiner

200

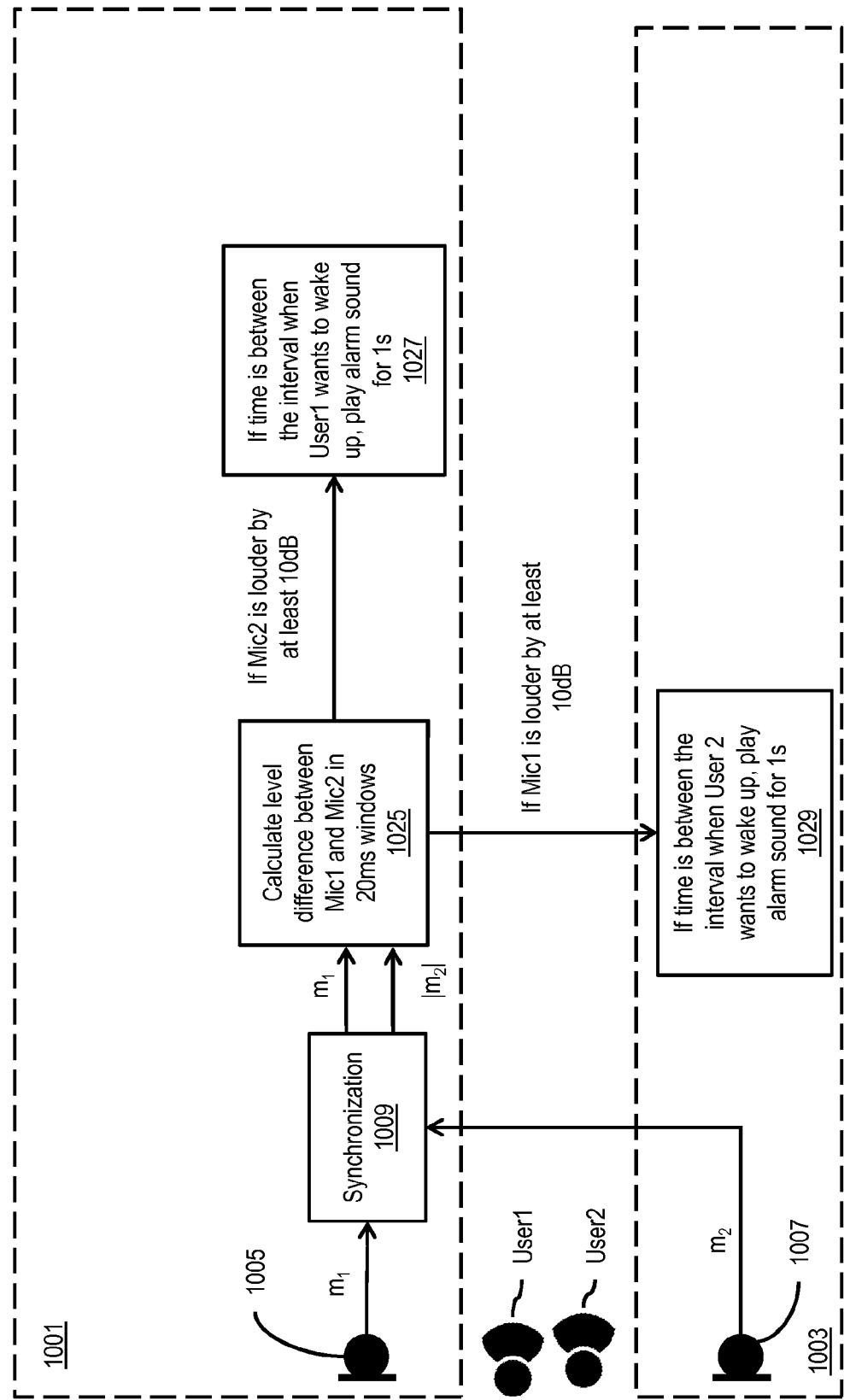

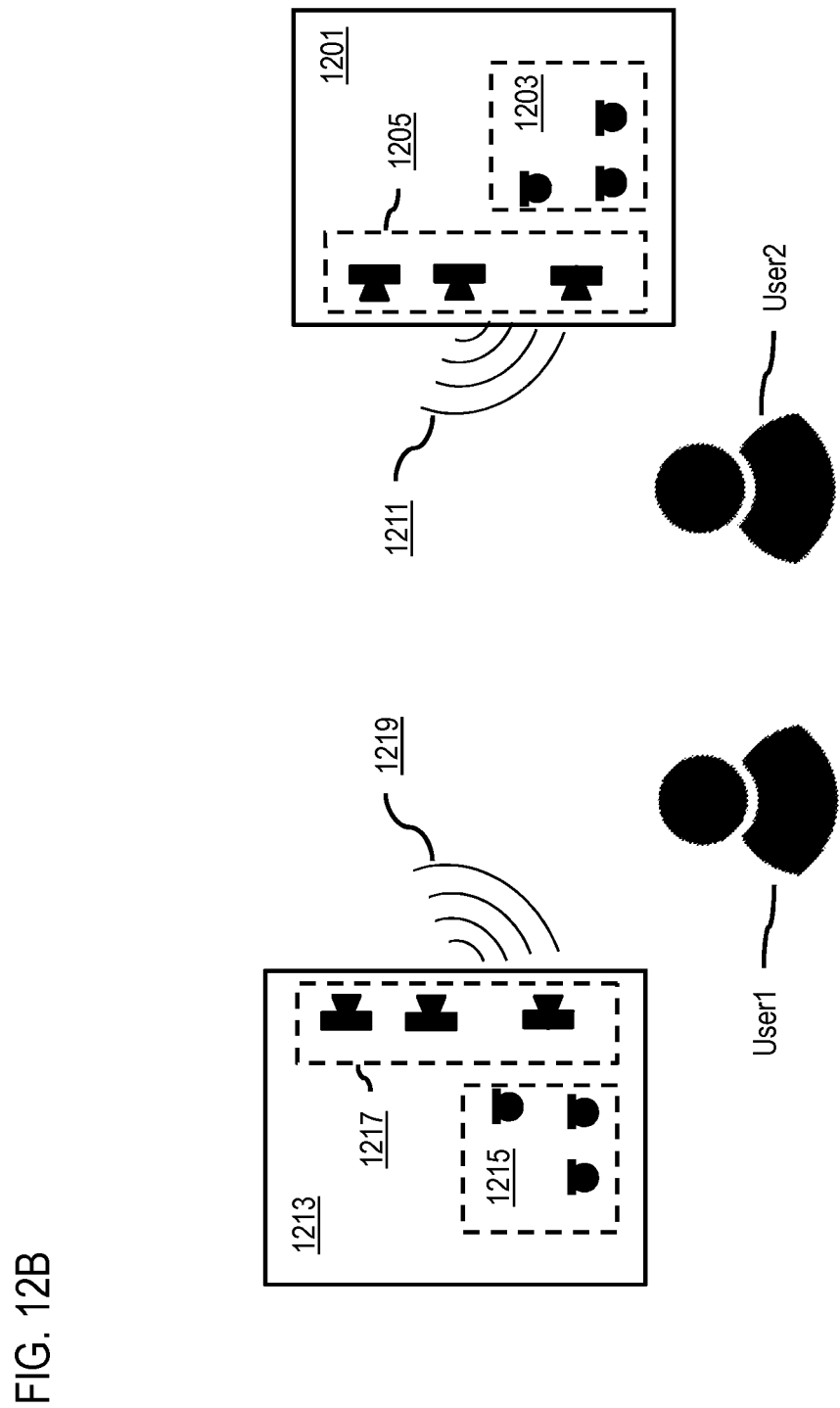

METHOD AND APPARATUS FOR PROVIDING AN INTELLIGENT ALARM NOTIFICATION

BACKGROUND

Typically, alarm systems utilize various sensors (e.g., microphones) to adjust and/or personalize the notification for a user. Unfortunately, the alarm systems while notifying a user may disrupt other users in the nearby vicinity. Since the alarm systems do not acknowledge the sleeping attributes of nearby users to adjust the alarm properties (e.g., volume levels, alarm timings, etc.) the notifications are not efficient, and are not appropriately directed towards the intended user.

SOME EXAMPLE EMBODIMENTS

Therefore, there is a need for an approach for providing alarm notification to the intended user while minimizing disturbance to the nearby users.

According to one embodiment, a method comprises determining sensor information associated with at least one first user and at least one second user collected while the at least one first user and the at least one second user are asleep. The method also comprises processing and/or facilitating a processing of the sensor information to determine sleep characteristic information for the at least one first user, the at least one second user, or a combination thereof. The method further comprises determining one or more alarm notification parameters for one or more alarm notifications based, at least in part, on the sleep characteristic information to direct the one or more alarm notifications to the at least one first user while minimizing a disturbance of the at least one second user.

According to another embodiment, an apparatus comprises at least one processor, and at least one memory including computer program code for one or more computer programs, the at least one memory and the computer program code configured to, with the at least one processor, cause, at least in part, the apparatus to determine sensor information associated with at least one first user and at least one second user collected while the at least one first user and the at least one second user are asleep. The apparatus is also caused to process and/or facilitate a processing of the sensor information to determine sleep characteristic information for the at least one first user, the at least one second user, or a combination thereof. The apparatus is further caused to determine one or more alarm notification parameters for one or more alarm notifications based, at least in part, on the sleep characteristic information to direct the one or more alarm notifications to the at least one first user while minimizing a disturbance of the at least one second user.

According to another embodiment, a computer-readable storage medium carries one or more sequences of one or more instructions which, when executed by one or more processors, cause, at least in part, an apparatus to determine sensor information associated with at least one first user and at least one second user collected while the at least one first user and the at least one second user are asleep. The apparatus is also caused to process and/or facilitate a processing of the sensor information to determine sleep characteristic information for the at least one first user, the at least one second user, or a combination thereof. The apparatus is further caused to determine one or more alarm notification parameters for one or more alarm notifications based, at least in part, on the sleep characteristic information to direct the one or more alarm notifications to the at least one first user while minimizing a disturbance of the at least one second user.

According to another embodiment, an apparatus comprises means for determining sensor information associated with at least one first user and at least one second user collected while the at least one first user and the at least one second user are asleep. The apparatus also comprises means for processing and/or facilitating a processing of the sensor information to determine sleep characteristic information for the at least one first user, the at least one second user, or a combination thereof. The apparatus further comprises means for determining one or more alarm notification parameters for one or more alarm notifications based, at least in part, on the sleep characteristic information to direct the one or more alarm notifications to the at least one first user while minimizing a disturbance of the at least one second user.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing a method of any of the claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIG. 10B is a diagram that represents a scenario wherein an alarm notification is adjusted based, at least in part, on synchronization of microphone signals, according to one example embodiment;

FIG. 12B is an illustration of using two speaker arrays and two microphone arrays to detect both user directions and to direct sounds to either user, according to one example embodiment;

DESCRIPTION OF SOME EMBODIMENTS

Examples of a method, apparatus, and computer program for providing intelligent alarm notifications are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Although various embodiments are described with respect to mobile phones, it is contemplated that the exemplary methods and systems described herein may be used in connection with any other electronic alarm device, for example, a smart watch, wearable devices, or any other alarm clock. The alarm functionality could be incorporated in any suitable electronic device such as a personal computer, a surveillance device, a robot, an automatic home assistant, an electric toy, a hi-fi system, a gaming console, or the like.

Figure 1:
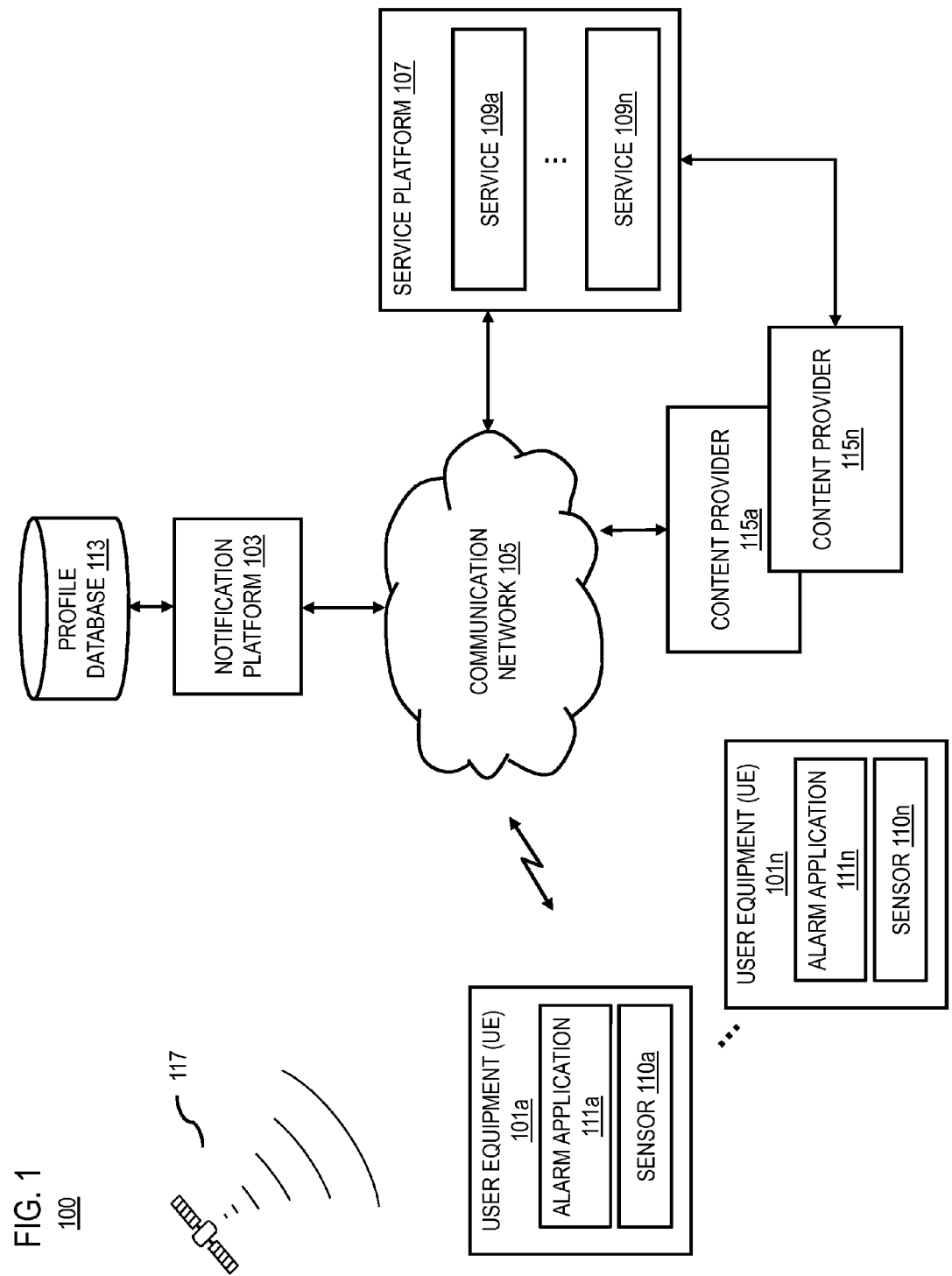
FIG. 1 is a diagram of a system for providing intelligent alarm notifications, according to one embodiment.

FIG. 1 is a diagram of a system for providing intelligent alarm notifications, according to one embodiment. For the purpose of illustration herein, the intelligent alarm notifications may pertain to any notification presented (or to be presented) by an electronic device based on alarm time, alarm duration, sleep quality of a user etc. This may include, for example, a sound of alarm, a message, a vibration or movement of the electronic device, etc.

As discussed previously, alarm notifications may be personalized for a user and may be generated based on information collected from various sensors. For example, the sound level of a user's breathing may be captured by a microphone of the user's device. Typically, the alarm notification time may then be accordingly adjusted for the user. Unfortunately, current alarm notification systems are not effective in situations where more than one person is sleeping in vicinity (e.g., friends or spouse sharing a room). In such a situation, the person other than the intended user of the alarm is disturbed by the alarm notifications. Therefore, the current alarm notification systems are not effective and may be problematic for people sharing a room.

To address this issue, a system 100 of FIG. 1 enables an alarm clock, i.e., as used by an electronic device (e.g., a mobile phone, a smart watch, an alarm clock etc.), to estimate the sleep quality of users and accordingly provide alarm notifications. In addition, the system 100 enables receiving and processing of sleep information of the users for estimating a suitable moment of time to provide alarm notifications.

In one embodiment, the notification platform 103 interfaces with one or more user equipment (UE) 101a-101n (also collectively referred to as UE 101) configured with one or more alarm applications 111a-111n (also collectively referred to as alarm module 111) over a communication network 105. The UE 101 may correspond to a mobile device, or a wearable device associated with a user. The alarm applications 111 of the UE 101 acquire sleep characteristic information or the like regarding the sleep quality of the users. By way of example, alarm applications 111 at the UE 101 may act as a client for the notification platform 103 and perform one or more functions associated with the functions of the notification platform 103 by interacting with the notification platform 103 over the communication network 105.

In addition, the alarm module 111 may interact with various sensors 110a-110n (also collectively referred to as sensors 110) for receiving and analyzing data regarding the commands from user, sleep characteristic information of the users, position or location of the user etc. By way of example, sensors 110 (e.g., of a mobile device or embedded within an alarm clock) may be used as GPS receivers for interacting with one or more satellites 117 for determining position and location data associated with the user. In addition, the sensors may gather position data (e.g., a sleep position or direction of the user), light data, sound data, image data, weather data, temporal data and the like associated with the users and/or UEs 101 thereof. Still further, the sensors 110 may detect local or transient network and/or wireless signals, such as those transmitted by nearby devices (e.g., another UE 101 in the room). It is further noted, in certain implementations, that the sensors 110 may operate in connection with each other for enabling data exchange and interaction. This exchange may be facilitated by way of any known or still developing range based or wireless communication protocols.

As will be discussed further, the notification platform 103 enables the UE 101 to provide alarm notifications based, at least in part, on the current sensor data as well as prior collected user data (e.g., voice commands, alarm time, or positions of the users). In one embodiment, the notification platform 103 monitors and receives data, referred to herein as sleep characteristic information, for estimating sleep quality of the users and providing alarm notifications from the UE 101. The sleep characteristic may include, for example, breathing sounds of the users, voice command of a user for setting up the alarm, direction of sound from which the voice command is received, directions of sound from which the breathing sounds are received, alarm notification time, etc. In one embodiment, the notification platform 103 stores the gathered data of sleep characteristic information to a profile database 113 for subsequent analysis.

In one embodiment, the notification platform 103 processes the sleep characteristic information, for generating alarm notification parameters. The alarm notification parameters may include, for example, an alarm time, alarm duration, direction of alarm notification, pattern of alarm notification, level of alarm notification, etc. In one embodiment, the notification platform 103 processes the voice commands received from a user to generate the alarm time, alarm duration, or direction of alarm notification. By way of example, the user may provide a voice command such as "Wake me up between 6:30 and 7 O' clock". In this case, one or more speech processing techniques are used to determine the alarm time as 6:30 AM, and alarm duration during which the notification is to be generated as 30 minutes. Further, the direction is detected based on beamforming of the voice command. In addition, the direction may be detected based on the breathing sounds of the users.

In one embodiment, the notification platform 103 processes the breathing sounds to synchronize them and the remove any undesired sound/noise. For example, the undesired sound/noise includes environmental noise, noise from movement or turning of the users in the bed, etc. are removed to generate normalized breathing sounds. The synchronization of the breathing sounds from the users enables effective processing of the breathing sounds. For example, the breathing sounds from different users received at different times at the notification platform 103 may be synchronized before further processing. Further, the notification platform 103 determines a difference between the breathing sound levels of the users. By way of example, the difference is calculated by aggregating the sound level information over predefined time duration in form of sound segments, and then applying statistical analysis on the levels of these segments. For example, the breathing sounds are gathered in segments of 20 milliseconds each and then top 10% of the segments that have the largest difference are used for calculating an average difference.

In one embodiment, the notification platform 103 generates alarm notifications based on the calculated difference. For example, for an alarm intended for a user of UE 101b, if breathing sound level of user at UE 101a is greater from a user at UE 101b by 6 dB, then alarm notification is generated at UE 101b. In a scenario where the UE 101a and the UE 101b are nearby, both the UEs 101a and 102b may capture breathing sounds from users of both the UEs 101a and 101b. Therefore, the notification platform 103 separates the breathing sounds of the UEs 101a and 101b. In an embodiment, the notification platform 103 uses the average difference to separate the breathings sounds and thus generate sleeper sounds.

Still further, the notification platform 103 estimates breathing parameters of the users by processing the sleeper sounds. For example, the breathing parameters include breathing sound levels and rhythm of breathing of the users. As such, the notification platform 103 generates alarm notifications based on the breathing rhythm of the users. By way of example, if from the breathing rhythm it is determined that the user at UE 101b is generating breathing sounds (or will be generating breathing sounds) at a time "t" (e.g., at 6:40 AM which is between the alarm duration of 6:30 AM and 7:00 AM) while the user at UE 101a is quiet (or will be quiet), then the alarm notification intended for the UE 101a are provided at that time.

In one embodiment, the notification platform 103 estimates sleep parameters of the users for processing the sleeper sounds. For example, the sleep parameters include an indication of deep sleep, light sleep, or snoring of the users. In this case, the notification platform 103 generates alarm notifications based on the sleep parameters/sleep pattern of the users. By way of example, if from the sleep parameters it is determined that the user at UE 101b is sleeping deeply or will be sleeping deeply) at a time "t" (e.g., at 6:40 AM which is between the alarm duration of 6:30 AM and 7:00 AM) while the user at UE 101a is sleeping lightly (or will be sleeping lightly), then the alarm notification intended for the UE 101a are provided at that time.

Further, the notification platform 103 generates visualization of the sleep parameters. For example, the visualization may be in form of graphical charts, line chart, bar chart, and the like. In one embodiment, the visualization enables generation of alarm notification.

In one embodiment, the alarm notifications are provided based on the direction of the intended user for the alarm. For example, the sound beam of the alarm notification is directed to the intended user to cause least disturbance to the other users. As noted previously, the direction may be detected based on analysis of the breathing sounds, the voice command, or other user sounds like turning in the bed or their combination.

While not shown expressly in FIG. 1, the service platform 107 and content providers 115 may also interact with the profile database 113 for retrieving location data of users, position data of users, historic sleep characteristic of the users, voice commands of the users, etc. It is noted that the notification platform 103 may be configured to operate in connection with any known alarm devices for enabling the initiation of instructions to be executed by the alarm devices, by a user of an alarm device, or a combination thereof. This may include, for example, a mobile phone having applications 111. Under this scenario, the mobile phone may communicate with other mobile phones configured to interact with the notification platform 103. As such, the notification platform 103 may determine optimal time or moment, type of notification, direction of the notification, or the like with respect to an alarm duration configured by the user.

By way of example, the notification platform 103 may be implemented as a cloud based service, hosted platform or the like for exchanging as well as receiving information from the services 109 of service platform 107, providers 115 or alarm applications 111. Alternatively, the notification platform 103 may be directly integrated for processing data generated and/or provided by the services 109, providers 115 or applications 111. Per this integration or interface, the notification platform 103 may process sleep characteristic information into useful data for providing intelligent alarm notifications.

By way of example, the communication network 105 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, surveillance device, robot, personal health device such as a blood pressure monitor or any combination thereof, including the accessories and peripherals of these devices, or any combination thereof. It is also contemplated that the UE 101 can support any type of interface to the user (such as "wearable" circuitry, etc.).

By way of example, the UEs 101, the notification platform 103, the service platform 107, and the content providers 115 communicate with each other and other components of the communication network 105 using well known, new or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
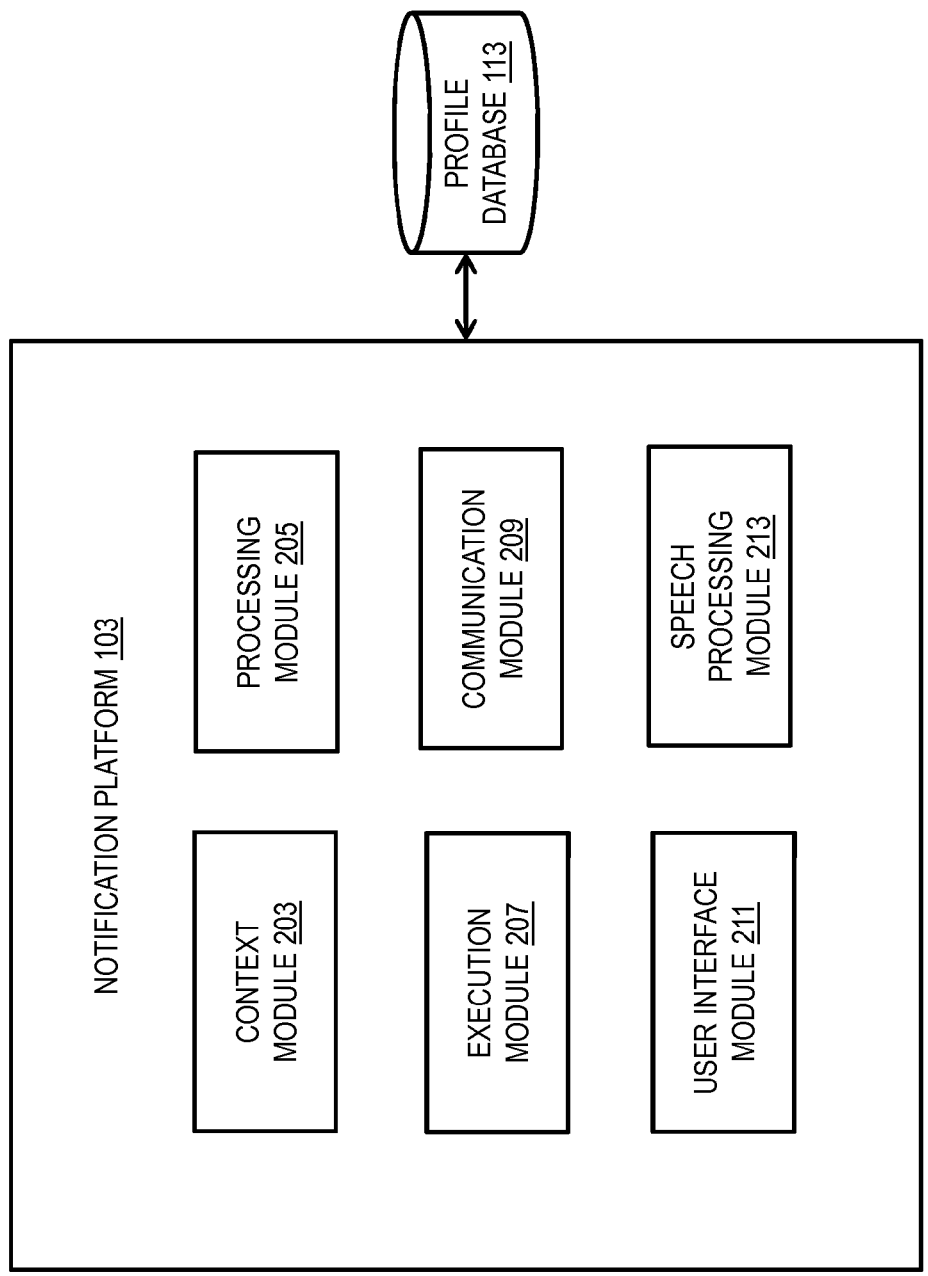
FIG. 2 is a diagram of the components of the notification platform 103, according to one embodiment.

FIG. 2 is a diagram of the components of the alarm module 111/notification platform 103, according to one embodiment. By way of example, the notification platform 103 includes one or more components for providing intelligent alarm notifications. It is contemplated that the functions of these components may be combined in one or more components or performed by other components of equivalent functionality. In this embodiment, the notification platform 103 includes a processing module 205, a context module 203, an execution module 207, a communication module 209, a user interface module 211, and a speech processing module 213.

The context module 203 gathers sleep characteristic information captured by sensors 110. As also previously noted, the sensors 110 include, but are not limited to, microphone, GPS etc., of the UE 101. As previously noted, the sleep characteristic information include breathing parameters of each user, voice command, direction of voice command, other sleeping sounds like movements (e.g., turning) in the bed, alarm notification time, or a combination thereof.

Examples of breathing parameters include, but are not limited, to sound level and rhythm of breathing. The processing module 205 operates in connection with the context module 203 to interpret the sleep characteristic information associated with the UE 101. By way of example, the processing module 205 works with the speech processing module 213 to recognize voice commands presented by the users. For example, a user voice command "Wake me up at 6:30 AM" is processed by the speech processing module 213 to setup an alarm time of 6:30 AM. Further, the processing module 205 operates in connection with the communication module 209 to receive sleep characteristic information from other UE 101. Further, the communication module 209 enables communication over the communication network 105. In one embodiment, the processing module 205 stores the gathered data of sleep characteristic information to a profile database 113 for subsequent analysis. In another embodiment, the processing module 205 stores and retrieves location data, position data, or other historical data related to the users in the profile database 113.

The execution module 207 determines an instruction, an action and/or a decision point to be executed by the UE 101 based on the sleep characteristic information. By way of example, the execution module 207 estimates rhythm of breathing for the users, quality of sleep of the users, and accordingly adjusts the alarm notification parameters. In one embodiment, the alarm notification parameters include, but are not limited to, an alarm time, direction of alarm notification, pattern of alarm notification, level of alarm notification, or a combination thereof. Per this execution, current actions may be executed, prioritized, or queued for initiation at the UE 101 based on the alarm notification parameters.

The execution module 207 may also operate in connection with the communication module 209 and user interface module 211 to cause the communication or rendering of an instruction respectively. By way of example, the execution module 207 may trigger the user interface module 211, which executes one or more application programming interface (API) executions of the notification platform 103 for presenting the alarm notification (i.e., sound, light, or vibration, etc.). In one embodiment, the user interface module 211 may generate visualization of one or more sleep characteristic information for one or more users. In one scenario, the visualization may be in form of a graph such as, but not limited to, a line graph, a bar graph, a histogram etc. By way of example, the visualization may enable determination of the status of sleep for one or more users (e.g., slower rhythm may be represented as a smaller value on the graph). As another example, the execution module 207 may trigger the communication module 209 to communicate an instruction for initiating the execution of alarm notification on other UE 101 based on the information contained in sleep characteristic.

The above presented modules and components of the notification platform 103 can be implemented in hardware, firmware, software, or a combination thereof. As such, the notification platform 103 may interact with the operating system or applications of the UE 101. In another embodiment, one or more of the modules 203-211 may be implemented separately for operation by respective UEs.

Figure 3:
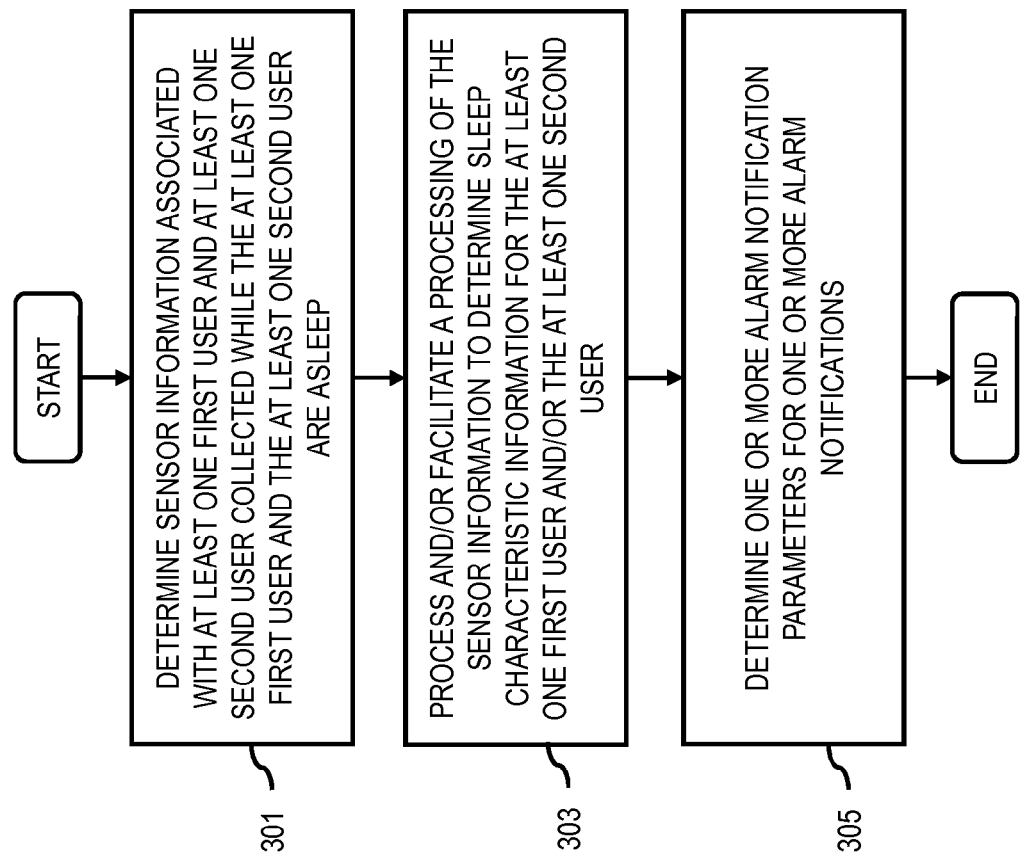
FIG. 3 is a flowchart of a process for channeling alarm notifications to the intended user while minimizing disturbance to the nearby users based, at least in part, on sleep characteristic information, according to one embodiment.
Figure 14:
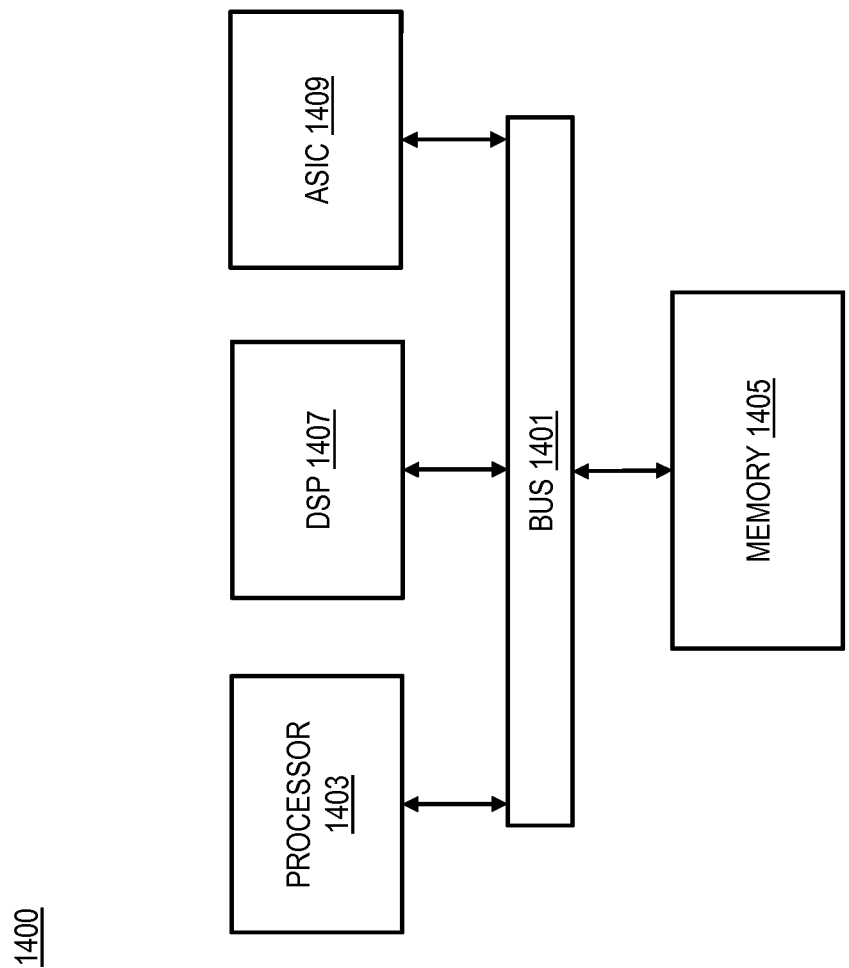
FIG. 14 is a diagram of a chip set that can be used to implement an embodiment of the invention.

FIG. 3 is a flowchart of a process for channeling alarm notifications to the intended user while minimizing disturbance to the nearby users based, at least in part, on sleep characteristic information, according to one embodiment. In one embodiment, the notification platform 103 performs the process 300 and is implemented in, for instance, a chip set including a processor and a memory as shown in FIG. 14.

In step 301, the notification platform 103 may determine sensor information associated with at least one first user and at least one second user collected while the at least one first user and the at least one second user are asleep. In one scenario, the notification platform 103 may receive sleep characteristic information for plurality of users via one or more sensors 110.

In step 303, the notification platform 103 may process and/or facilitate a processing of the sensor information to determine sleep characteristic information for the at least one first user, the at least one second user, or a combination thereof. In one embodiment, the sleep characteristic information includes at least one first breathing rhythm, at least one second breathing rhythm, at least one first sleeping pattern, at least one second sleeping pattern, or a combination thereof. In one scenario, the notification platform 103 may remove sound information except the breathing sounds of the one or more users via filtering (e.g. removing audio signal content outside a frequency range of 200 Hz-3400 Hz), segmenting the audio signal to 20 ms segments and using audio classification to recognize segments with breathing sounds and silencing other segments or using audio object separation. A person skilled in the art will appreciate that any other audio processing technique may be used to identify and filter the breathing sounds.

In step 305, the notification platform 103 may determine one or more alarm notification parameters for one or more alarm notifications based, at least in part, on the sleep characteristic information to direct the one or more alarm notifications to the at least one first user while minimizing a disturbance of the at least one second user. In one embodiment, the alarm notification parameters may include alarm time, direction of alarm notification, pattern of alarm notification, level of alarm notification, sleep characteristic information for the plurality of users, or a combination thereof. In another embodiment, the alarm notification may include a sound, a vibration, a display, or a combination thereof. By way of example, the alarm notifications are generated when an intended user for the alarm is making less sound than the other users. Further, the rhythm of the alarm notification may be based on the breathing level of one or more users.

Figure 4:
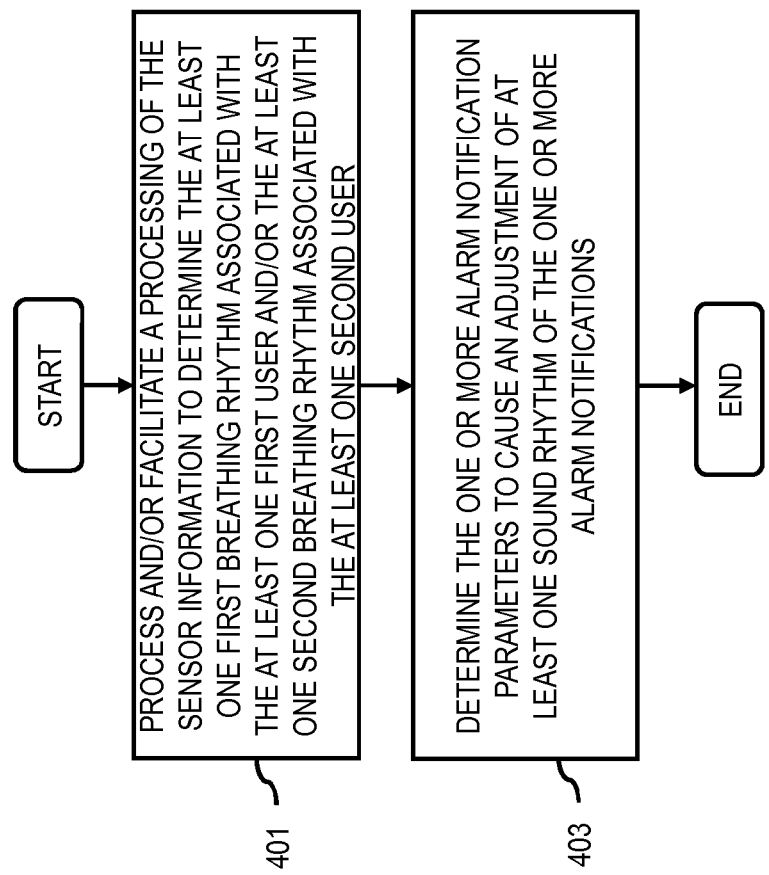
FIG. 4 is a flowchart of a process for causing an adjustment in the sound rhythm of an alarm notification based, at least in part, on the breathing rhythm associated with one or more users, according to one embodiment.

FIG. 4 is a flowchart of a process for causing an adjustment in the sound rhythm of an alarm notification based, at least in part, on the breathing rhythm associated with one or more users, according to one embodiment. In one embodiment, the notification platform 103 performs the process 400 and is implemented in, for instance, a chip set including a processor and a memory as shown in FIG. 14.

In step 401, the notification platform 103 may process and/or facilitate a processing of the sensor information to determine the at least one first breathing rhythm associated with the at least one first user, the at least one second breathing rhythm associated with the at least one second user, or a combination thereof. In one example embodiment, the notification platform 103 may process the breathing rhythm for one or more users to determine sleep parameters. The sleep parameters may include a status of deep sleep, a status of light sleep, a status of snoring, etc. Then, the notification platform 103 may cause an alarm notification based, at least in part, on the sleep parameters.

In step 403, the notification platform 103 may determine the one or more alarm notification parameters to cause, at least in part, an adjustment of at least one sound rhythm of the one or more alarm notifications to match the at least one second breathing rhythm for the alarm notifications directed to the at least one first user. In one example embodiment, the notification platform 103 may detect that user A is snoring. Then, the notification platform 103 may wake user A by timing the alarm, so that it occurs when the non-snoring user is making sounds and the snoring user is quiet. Alternatively, the alarm may be directed towards the direction of the snoring user. In another embodiment, if a user is soundly asleep and is quiet, the notification platform 103 may utilize user movements in the bed (e.g., turning of the users in the bed) for detecting the direction of the users and their sleeping patterns.

Figure 5:
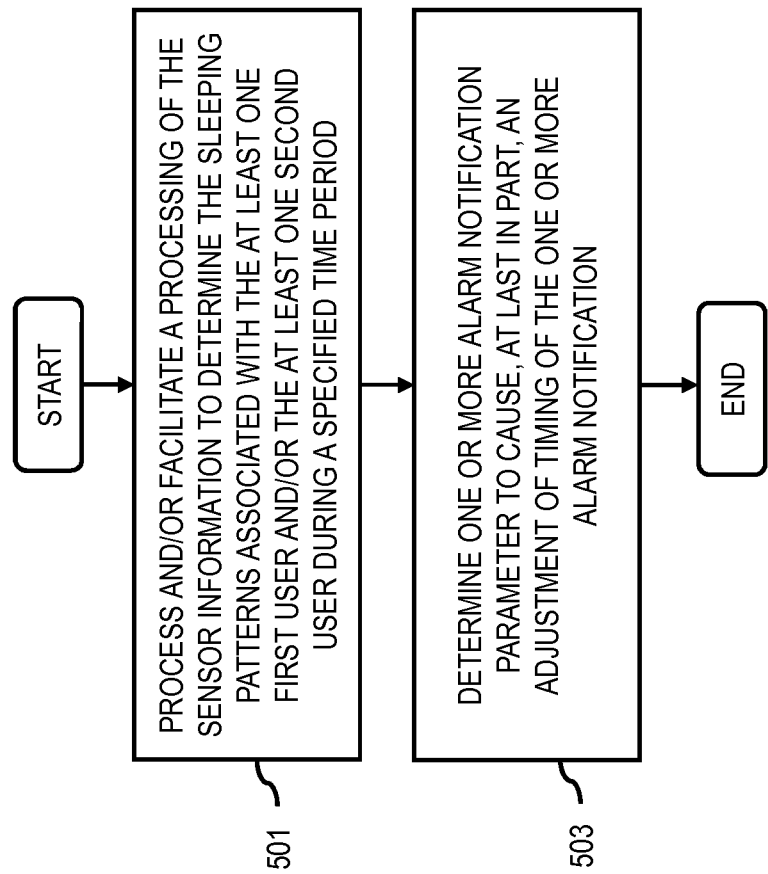
FIG. 5 is a flowchart of a process for causing an adjustment in the timing of the one or more alarm notifications based, at least in part, on the sleeping patterns of one or more users, according to one embodiment.

FIG. 5 is a flowchart of a process for causing an adjustment in the timing of the one or more alarm notifications based, at least in part, on the sleeping patterns of one or more users, according to one embodiment. In one embodiment, the notification platform 103 performs the process 500 and is implemented in, for instance, a chip set including a processor and a memory as shown in FIG. 14.

In step 501, the notification platform 103 may process and/or facilitate a processing of the sensor information to determine the at least one first sleeping pattern associated with the at least one first user, the at least one second sleeping pattern associated with the at least one second user, or a combination thereof during a specified time period. In one example embodiment, user A makes adjusts an alarm setting between 6:30 and 7:00. Then, the notification platform 103 may find the best moment between 6:30 and 7:00 to wake user A. In one scenario, the best moment is when user A is sleeping lightly and user B is sleeping heavily.

In step 503, the notification platform 103 may determine one or more alarm notification parameter to cause, at last in part, an adjustment of timing of the one or more alarm notification to match the at least one second sleeping pattern for the alarm notifications directed to the at least one first user. In one scenario, the notification platform 103 may cause an adjustment in the timing of the alarm of user A so that is occurs when user A is sleeping lightly and user B is sleeping deeply henceforth making sure that user B less likely to be disturbed by the alarm that is meant for user A. In another scenario, the best moment to wake a user within the fixed time interval is when the intended user sleeps the lightest and the other nearby users sleep the deepest. However, if the intended user is in a deep sleep, and the nearby user is in a light sleep, the notification platform 103 may decide to wait for a better moment to wake the intended user. The wait may exceed the fixed time period by the user.

Figure 6:
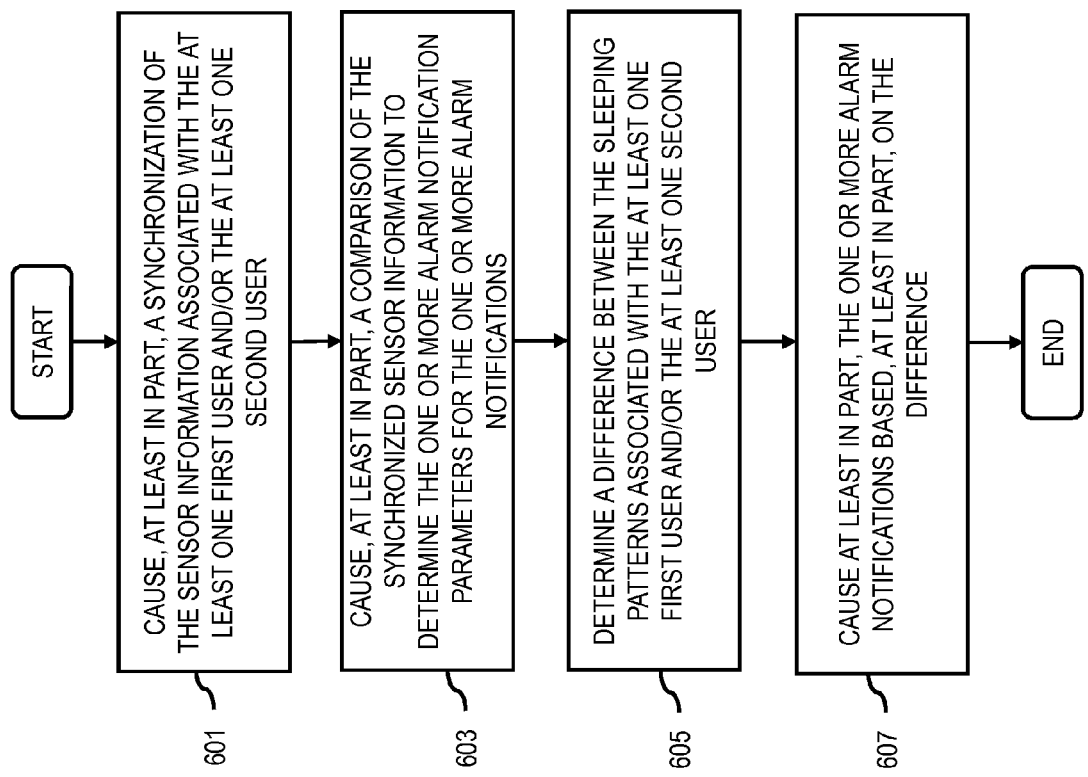
FIG. 6 is a flowchart of a process for comparing synchronized sensor information to determine a difference in sleep characteristic information for one or more users, according to one embodiment.

FIG. 6 is a flowchart of a process for comparing synchronized sensor information to determine a difference in sleep characteristic information for one or more users, according to one embodiment. In one embodiment, the notification platform 103 performs the process 600 and is implemented in, for instance, a chip set including a processor and a memory as shown in FIG. 14.

In step 601, the notification platform 103 may cause, at least in part, a synchronization of the sensor information associated with the at least one first user, the at least one second user, or a combination thereof.

In step 603, the notification platform 103 may cause, at least in part, a comparison of the synchronized sensor information to determine the one or more alarm notification parameters for the one or more alarm notifications. In one scenario, the notification platform 103 may synchronize two microphone signals by finding a time delay that produces maximum correlation between the sleep characteristic information for one or more users in the nearby vicinity. In one example embodiment, when UE 101 associated with the second user is significantly (e.g. 6 dB) louder than UE 101 associated with the first user, then the notification platform 103 may determine to sound an alarm to the first user for a brief time.

In step 605, the notification platform 103 may determine a difference between the at least one first sleeping pattern associated with the at least one first user, the at least one second sleeping pattern associated with the at least one second user, or a combination thereof. In one example embodiment, the notification platform 103 may determine the difference in noise level and/or body position of one or more users while sleeping to identify the one or more users within a proximate area (e.g., a room).

In step 607, the notification platform 103 may cause, at least in part, the one or more alarm notifications based, at least in part, on the difference. In one scenario, the notification platform 103 may generate one or more alarm notifications for at least one user based, at least in part, on the different sleep characteristic information of the proximate users. In one example embodiment, sleeper sounds may be enhanced by the notification platform 103 by using the determined difference. In one example embodiment, the notification platform 103 may cause an alarm notification within the time interval fixed by a user based, at least in part, on the difference between the sleeping patterns of one or more users. The best moment to wake user 1 is the moment within the fixed time interval and when the difference between the sleeping patterns of user 1 and user 2 is at its greatest, i.e., user 1 sleeps the lightest and user 2 the deepest.

Figure 7:
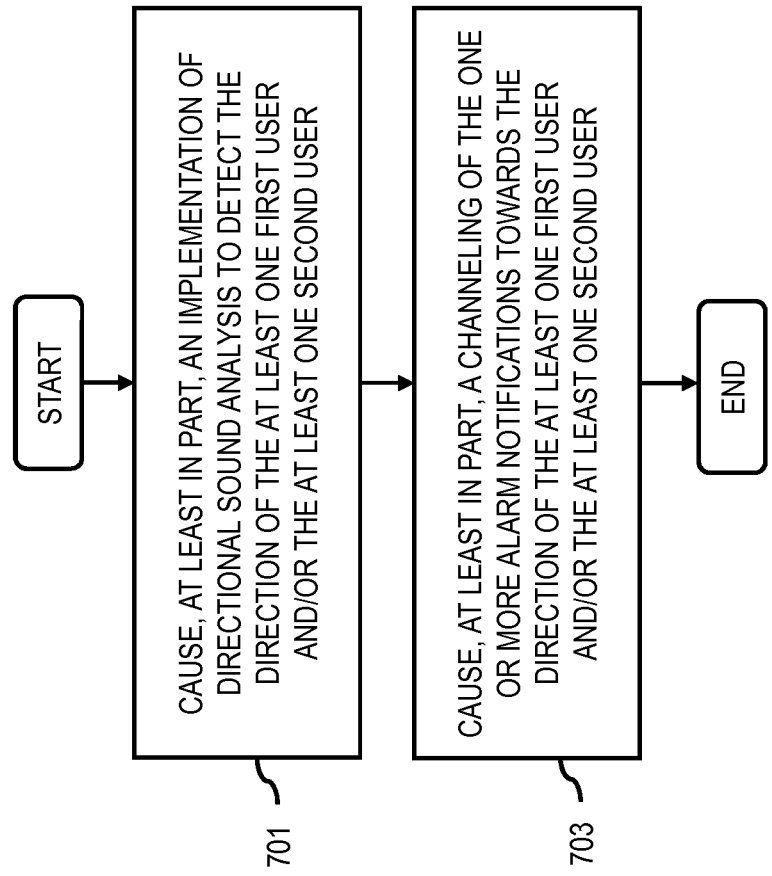
FIG. 7 is a flowchart of a process for channeling alarm notifications towards the direction of at least one user detected via directional sound analysis, according to one embodiment.

FIG. 7 is a flowchart of a process for channeling alarm notifications towards the direction of at least one user detected via directional sound analysis, according to one embodiment. In one embodiment, the notification platform 103 performs the process 700 and is implemented in, for instance, a chip set including a processor and a memory as shown in FIG. 14.

In step 701, the notification platform 103 may cause, at least in part, an implementation of directional sound analysis to detect the direction of the at least one first user, the at least one second user, or a combination thereof. In one scenario, direction microphones or beamforming may be used to focus on sounds from different directions. In one example embodiment, the notification platform 103 may use the relative distance and the relative levels of users' voices reaching the microphones to determine which parts of the sound belong to which user. In one scenario, with the microphone arrays (e.g., two or more microphones) the sound direction can be used to separate user sounds, and the alarm notification may be directed to the same direction from which the user sound was detected.

In step 703, the notification platform 103 may cause, at least in part, a channeling of the one or more alarm notifications towards the direction of the at least one first user, the at least one second user, or a combination thereof. In one embodiment, any of various known directional sound techniques may be used to channel one or more alarm notifications towards the destined user, thereby the disturbance to other users in the vicinity is reduced.

Figure 8:
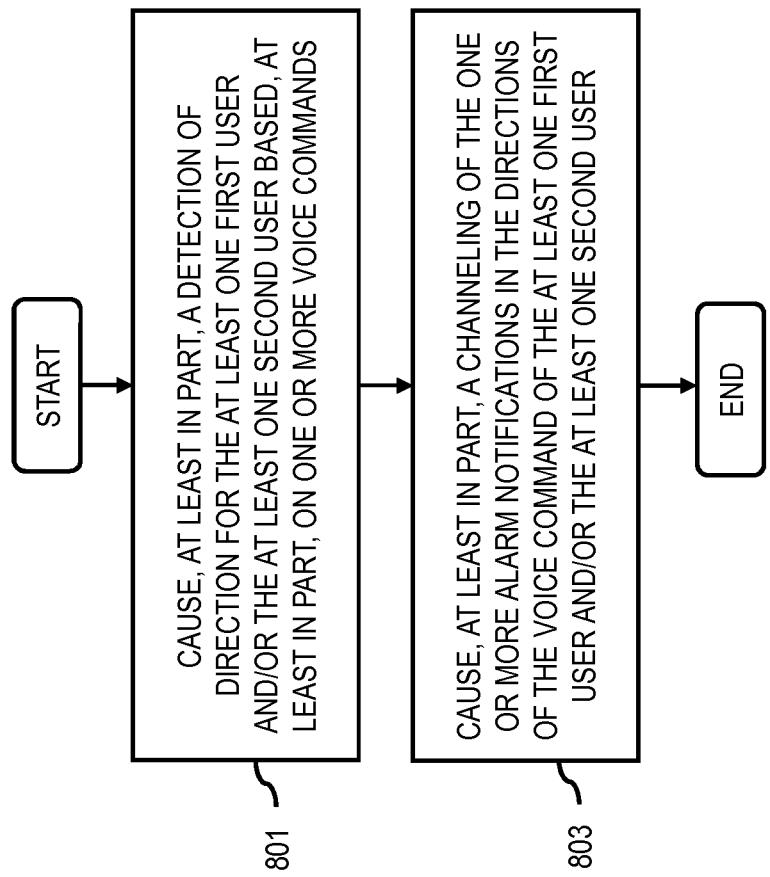
FIG. 8 is a flowchart of a process for channeling alarm notifications towards the direction of voice command by at least one user, according to one embodiment.

FIG. 8 is a flowchart of a process for channeling alarm notifications towards the direction of voice command by at least one user, according to one embodiment. In one embodiment, the notification platform 103 performs the process 800 and is implemented in, for instance, a chip set including a processor and a memory as shown in FIG. 14.

In step 801, the notification platform 103 may cause, at least in part, a detection of direction for the at least one first user, the at least one second user, or a combination thereof based, at least in part, on one or more voice commands. In one scenario, the notification platform 103 may receive a voice command from at least one user, wherein the voice command includes instructions for setting up an alarm notification (e.g., "Wake me between 6:30 and 7 O' clock"). Then, the notification platform 103 may process the voice command to cause, at least in part, a determination of a direction of the user. In one embodiment, the direction may be detected by beamforming the voice command. In one embodiment, any of various known beamforming techniques may be used to detect the direction.

In step 803, the notification platform 103 may cause, at least in part, a channeling of the one or more alarm notifications in the directions of the voice command of the at least one first user, the at least one second user, or a combination thereof.

Figure 9:
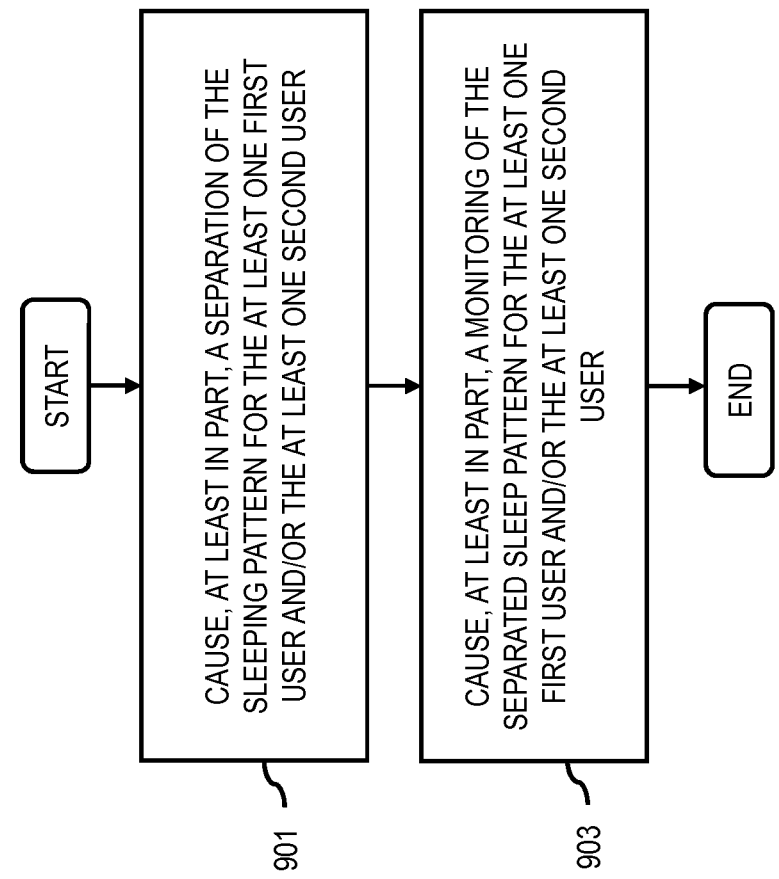
FIG. 9 is a flowchart of a process for monitoring the separated sleeping pattern for one or more users, according to one embodiment.

FIG. 9 is a flowchart of a process for monitoring the separated sleeping pattern for one or more users, according to one embodiment. In one embodiment, the notification platform 103 performs the process 900 and is implemented in, for instance, a chip set including a processor and a memory as shown in FIG. 14.

In step 901, the notification platform 103 may cause, at least in part, a separation of the sleeping pattern for the at least one first user, the at least one second user, or a combination thereof. In one scenario, the notification platform 103 may separate the sounds made by plurality of users. The separated sounds of one or more users while sleeping may be used for estimating the users' sleep patterns, for example, if user A is the noisiest, then he/she may have the biggest values on the graph depicting the sleeping patterns.

In step 903, the notification platform 103 may cause, at least in part, a monitoring of the separated sleeping pattern for the at least one first user, the at least one second user, or a combination thereof in real-time, periodically, according to schedule, on demand, or a combination thereof. In one scenario, the notification platform 103 may provide an individualized sleep pattern monitoring.

Figure 10A:
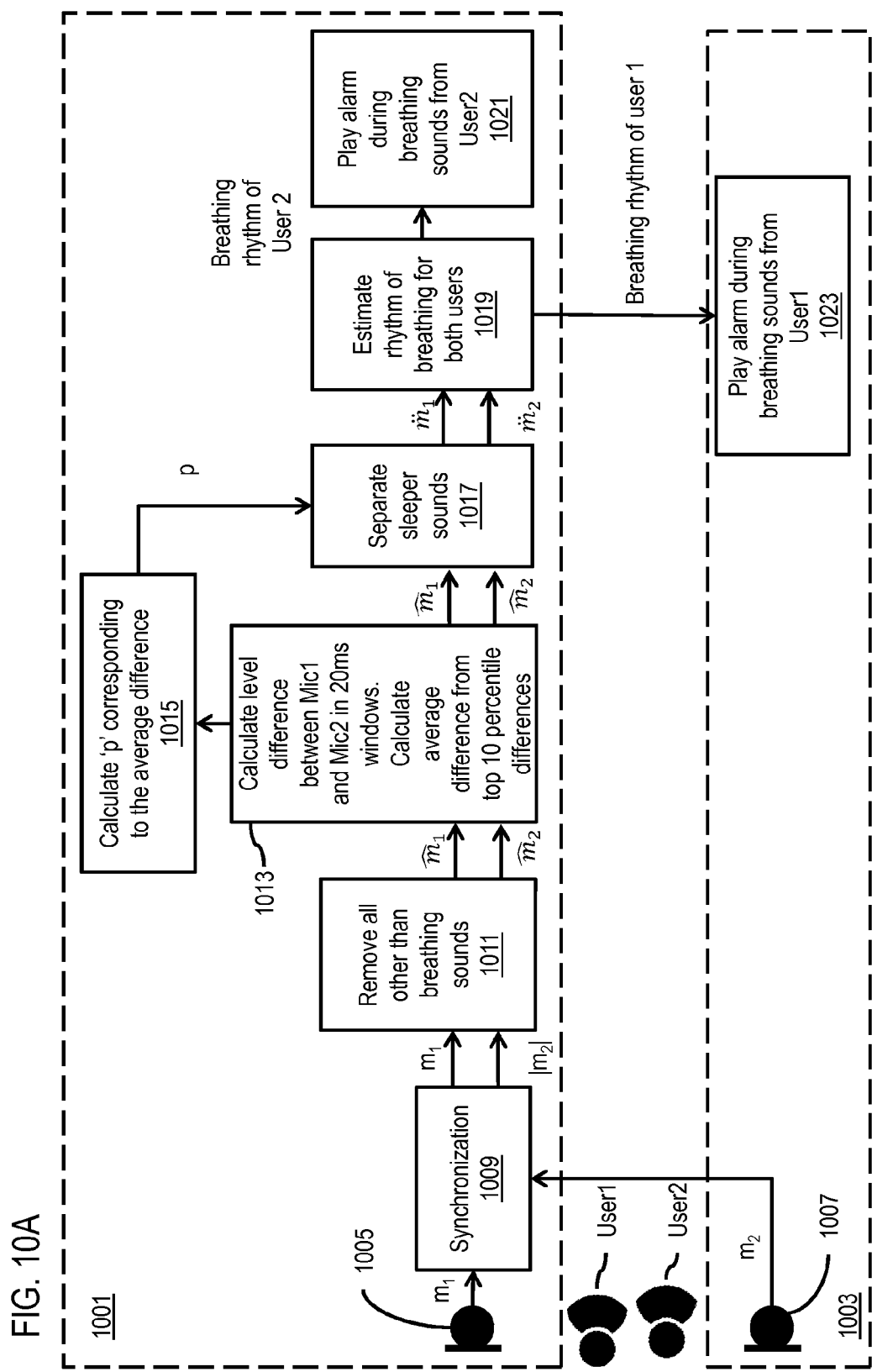
FIG. 10A is a diagram that represents a scenario wherein sound rhythm for an alarm notification is adjusted based, at least in part, on breathing rhythm of one or more users, according to one example embodiment.

FIG. 10A is a diagram that represents a scenario wherein sound rhythm for an alarm notification is adjusted based, at least in part, on breathing rhythm of one or more users, according to one example embodiment. FIGS. 10A and 10B include a UE 1001 corresponding to a User1, and a UE 1003 corresponding to a User2. In one embodiment, the UE 1001 and UE 1003 may be any of UE 101 and have the same functionalities or alarm module 111. As shown, the UE 1001 includes a Mic1 1005, and the UE 1003 includes a Mic2 1007 for capturing sounds 'm1' and 'm2' of the User1 and User2 respectively. By way of example, the sounds of the User1 and User2 (collectively referred to as the Users) include breathing sounds. In one embodiment, the Mic1 1005 and the Mic2 1007 capture sounds mostly from the User1 and User2 respectively. In another embodiment, the Mic1 1005 and the Mic2 1007 capture sounds, at least in part, from both the users. Further, the Mic1 1005 and the Mic2 1007 capture sounds from sources other than the users (e.g., environmental noise, turning of users, etc.).

At block 1009, the sound 'm2' captured by Mic2 is synchronized with the sound 'm1' to generate synchronized sleep characteristic information containing sounds 'm1' and '|m2|'. As previously discussed, the synchronization is performed by finding a time delay that produces maximum correlation between the 'm1' and 'm2'. In an embodiment, a synchronized clock signals from the UE 1001 and US 1003 may be used to generate the synchronized sleep characteristic information.

Thereafter, at block 1011, the sounds 'm1' and '|m2|' are processed to remove all sounds other than the breathing sounds of the User1 and User2, to generate normalized sleep information. The normalized sleep information for User 1 is depicted as $\hat{m}_1$, and for User 2 is depicted as $\hat{m}_2$ in FIG. 10A. As previously discussed, audio processing techniques may be used to generate the normalized sleep information.

Subsequently, at block 1013 and 1015, the sounds are enhanced by determining a difference in the normalized sleep information. In one embodiment, a difference in the levels of sounds $\hat{m}_1$ and $\hat{m}_2$ is determined. By way of example, signals $\hat{m}_1$ and $\hat{m}_2$ are divided into short segments of a predefined time interval (e.g., 20 ms). Thereafter, it is determined whether each segment contains mostly sounds from User1 or User2. For example, a segment contains mostly sounds from User1 if the segment is louder in Mid 1 1005 than in Mic2 1007. A level difference is then determined from several such segments. Then, a predefined percentage of these segments (e.g., 10% of the segments) that have the largest difference are used to calculate an average difference at block 1013. Thereafter, at block 1015, the average difference is used to calculate a value "p" that may represent an estimate of how much louder sounds from User1 arrive at UE 1001 than from User2. At block 1017, the value "p" can be used to generate sleeper sounds $\tilde{m}_1$ of User1 and $\tilde{m}_2$ of User2 by using the following equations:

$$\tilde{m}_1 = \frac{\hat{m}_2 - p\hat{m}_1}{1 - p^2} \qquad \text{Equation (1)}$$

$$\tilde{m}_2 = \frac{\hat{m}_1 - p\hat{m}_2}{1 - p^2} \qquad \text{Equation (2)}$$

In an embodiment, the notification platform 103 uses the average difference to separate the breathings sounds and thus generate sleeper sounds. As previously noted, in a scenario where the UE 1001 and the UE 1003 are nearby, both the UEs 1001 and 1003 may capture breathing sounds from users of both the User1 and User2. Therefore, the breathing sounds of the User1 and User2 are separated and enhanced by using the value "p" and the equations 1 and 2 above.

Per block 1019, the breathing parameters of the Users are estimated. As previously discussed, the breathing parameters include the breathing rhythm of the Users. The estimation includes a predicted time at which the breathing of the Users takes place. By way of example, if from the breathing rhythm it is determined that the User2 is generating breathing sounds (or will be generating breathing sounds) at a time "t" (e.g., at 6:40 AM which is between the alarm duration of 6:30 AM and 7:00 AM) while the User1 is quiet (or will be quiet), then the alarm notification intended for the User1 are provided at that time. Therefore, at block 1021, the alarm is played at UE 1001 during the breathing rhythm of User2. Hence, the User2 less likely to wake up for the alarm intended for User1. Similarly, if the alarm is intended for User2, then it is played at UE 1003 during breathing rhythm of User1 at block 1023. In one embodiment, for better effectiveness, the alarm notification sound has a rhythm that matches the breathing rhythm of a user.

FIG. 10B is a diagram that represents a scenario wherein an alarm notification is adjusted based, at least in part, on synchronization of microphone signals, according to one example embodiment. As depicted in FIG. 10B, at block 1025 a difference in the level of 'm1' and '|m2|' is determined over a predefined time interval (e.g., 20 milliseconds). Thereafter, based on a predefined threshold level (e.g., 10 dB) alarm notification is generated. At block 1027, the alarm is played at UE 1001 if '|m2|' is louder than 'm1' by the predefined threshold level during the alarm interval set by the User1. By way of example, if the User1 has set up the alarm interval from 10:30 AM to 7:00 AM, and the sound '|m2|' is louder by 10 dB from 'm1' (i.e., |m2|−m1 is more than 10 dB) at 10:40 AM, then the alarm is played at 10:40 AM for a predefined duration (e.g., 1 s). Similarly, the alarm notification is generated for UE 1003 at block 1029 when the alarm is intended for the User2 and the above discussed conditions are met. Further, the alarm notification may be repeated until the user turns the alarm off. This implementation depicted in FIG. 10B may be used in situations when there are other non-rhythmic sounds (e.g., turning of the users) along with the breathing sounds of the users.

In one embodiment, the UEs 1001 and 1003 communicate over the communication network 105. In another embodiment, the UEs 1001 and 1003 communicate wirelessly over a radio network such as, but not limited to, Bluetooth®, WiFi, cellular communication etc.

The processes described herein for providing intelligent alarm notifications may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed in conjunction with FIGS. 10 A-B.

Figure 11A:
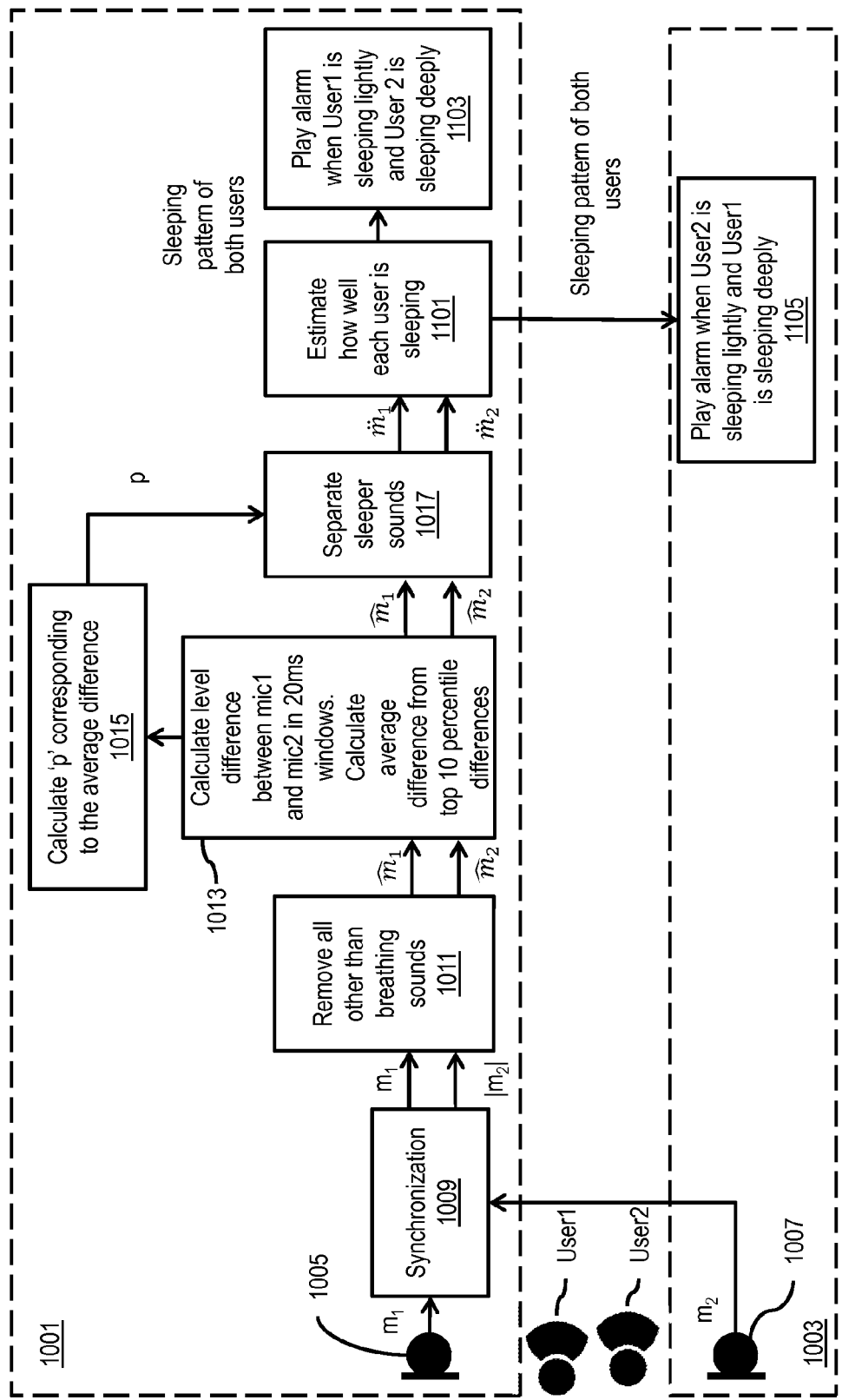
FIG. 11A is a diagram that represents a scenario wherein timing for an alarm notification is adjusted based, at least in part, on sleep characteristic information for one or more users, according to one example embodiment.
Figure 11B:
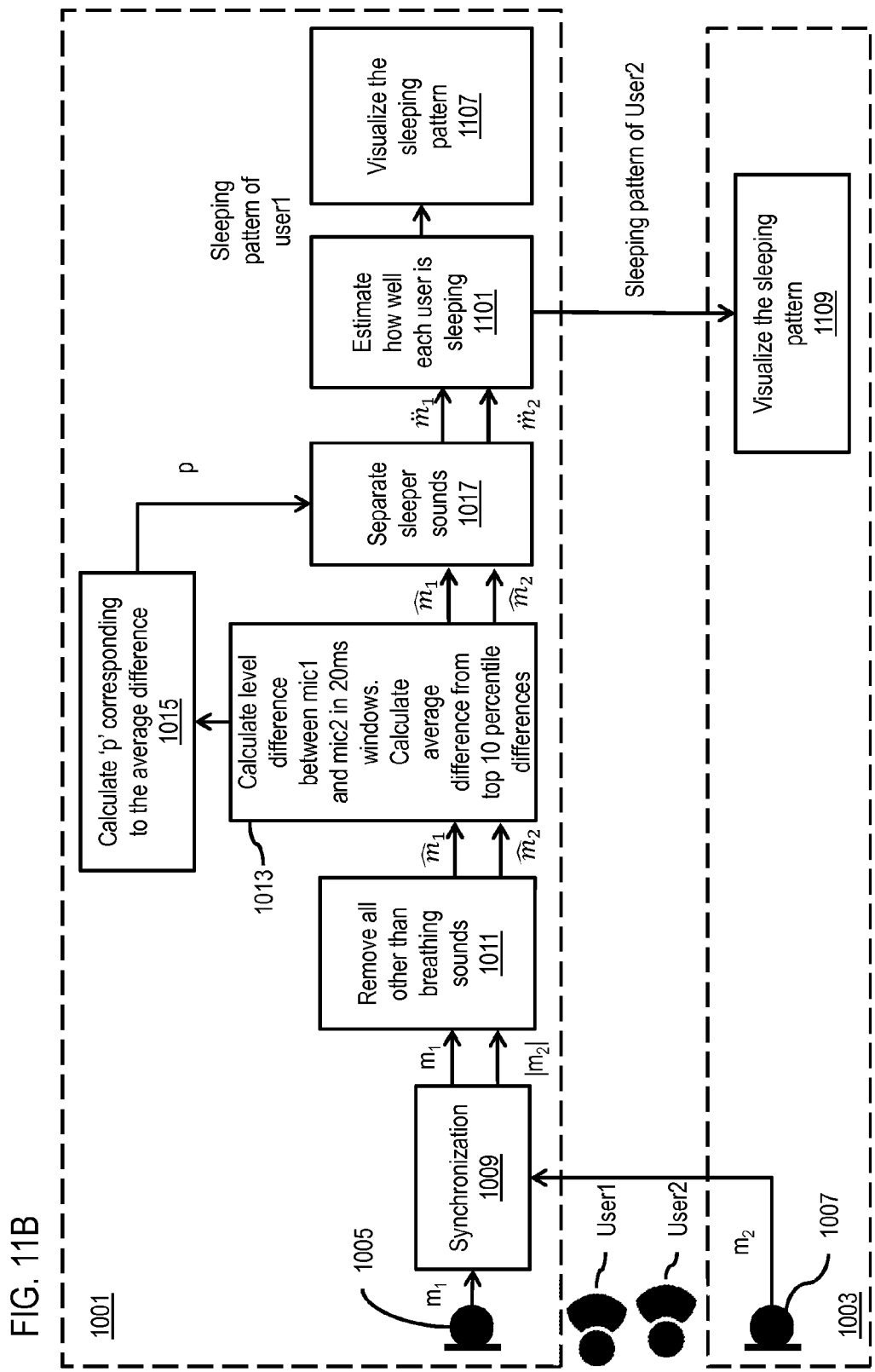
FIG. 11B is a diagram that visualizes the sleep pattern for one or more users based, at least in part, on sleep characteristic information, according to one example embodiment.

FIG. 11 A is a diagram that represents a scenario wherein timing for an alarm notification is adjusted based, at least in part, on sleep characteristic information for one or more users, according to one example embodiment. Typically, there are two types of sleep pattern for a user, i.e., sleeping lightly or sleeping deeply. Further, the sleeping patterns can be estimated by determining the noise level of breathing sounds or other user sounds. By way of example, a user is sleeping deeply when the noise is low and sleeping lightly when it is noisier than an average level. The alarm notifications are more effective when they are generated at a time when the intended user is sleeping lightly and the other user(s) are sleeping deeply. As depicted in FIGS. 11A and 11B, the sleeper sounds are separated at block 1017 following a similar process as discussed in FIG. 10A.

Thereafter, at block 1101 the sleep pattern or quality of sleep in estimated. The sleep pattern may then be used to estimate a time to wake up the user within the set alarm time duration (e.g., 6:30 AM to 7:00 AM). By way of example, within the set alarm time duration, if the level of breathing sound from the User1 is continuously increasing and that of the User2 is reducing, then alarm notifications are not presented till difference between the sleeping patterns of the User1 and the User2 is maximum (i.e., the User1 sleeps the lightest and the User2 the deepest based on the sound levels).

As shown, when the alarm is intended for the User1, the alarm notification are played at block 1103 when the User1 is sleeping lightly and the User2 is sleeping deeply. Similarly, at block 1105, the alarm notifications intended for the User2 are played when the User1 is sleeping deeply and the User2 is sleeping lightly.

FIG. 11 B is a diagram that visualizes the sleep pattern for one or more users based, at least in part, on sleep characteristic information, according to one example embodiment. As depicted in FIG. 11B, the sleep pattern may be used to generate visualization of the sleep patterns. In one embodiment, the visualization includes graphical representations including, but not limited to, a line graph, a bar graph, etc. At block 1107, the sleep pattern of the User1 is visualized when the sleep pattern shows that the User1 is sleeping lightly and the User2 is sleeping deeply. Similarly, at block 1109, the sleep pattern of the User2 is visualized when the sleep pattern shows that the User2 is sleeping lightly and the User1 is sleeping deeply. The visualization enables estimation of sleep characteristics or patterns such as periods of snoring etc. By way of example, if it is detected that User1 is snoring then the alarm notification may be provided between the snoring sounds to wake up the User1. Further, the alarm notification may be timed, so that the non-intended user (e.g., User2) is snoring and the User1 is not snoring or is quiet. In one embodiment, the alarm notifications may be directed towards the direction of the snoring user by directional audio techniques as explained in more detail in conjunction with FIGS. 8A and 8B. Therefore, the alarm notification cause least possible disturbance to the non-intended users.

Figure 12A:
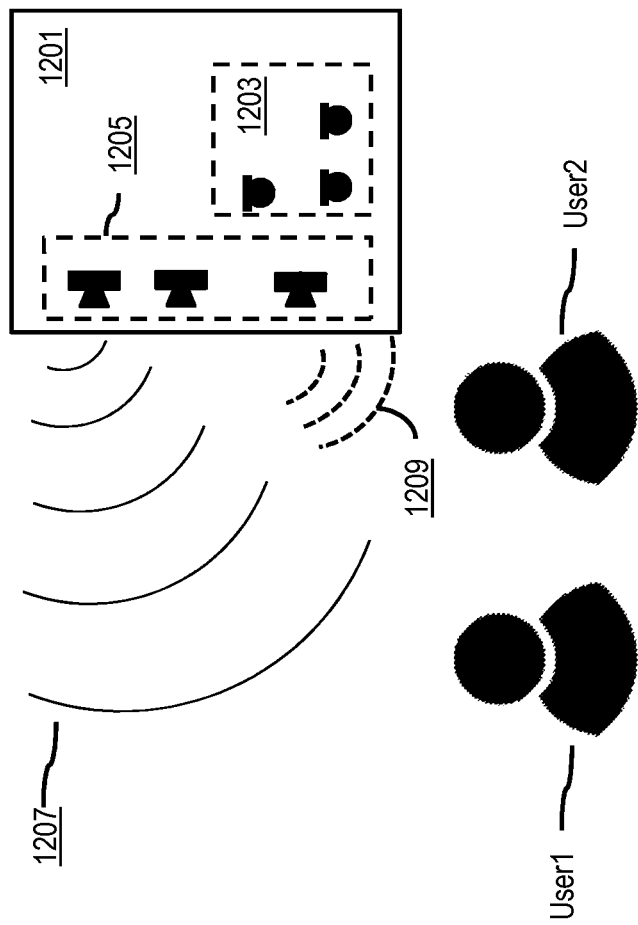
FIG. 12A is an illustration of using a single speaker array and a single microphone array to detect both user directions and to direct sounds to either user, according to one example embodiment.

FIG. 12 A is an illustration of using a single speaker array and a single microphone array to detect both user directions and to direct sounds to either user, according to one example embodiment. As shown in FIG. 12A, a UE 1201 may include a microphone array 1203 and a speaker array 1205 for detecting and directing sounds to a User1 and User2 (collectively referred to as users). The UE 1201 uses the microphone array 1203 to detect the direction of sounds. The alarm notifications may then be directed to the users by beam 1207 and beam 1209 based on the direction of the users.

FIG. 12 B is an illustration of using two speaker arrays and two microphone arrays to detect both user directions and to direct sounds to either user, according to one example embodiment. In FIG. 12B, the User1 and User2 may have a corresponding UE 1201 and UE 1213. UE 1213 uses a microphone array 1215 to detect the direction of the User1 and a speakers array 1217 to direct the alarm notifications as a beam 1219 in the same direction. Similarly, the UE 1201 directs the beam 1211 in the direction of the User2, as detected by the speaker array 1205. By way of example, a user may say "My Phone, set alarm from 6:30 to 7 O'clock". In this case, the user voice direction is detected by using the microphone arrays and the alarm time interval is determined by using directional audio analysis and speech recognition. Thereafter, the user sounds only from detected direction are captured (e.g., by using beamforming).

The processes described herein for providing alarm notification to the intended user while minimizing disturbance to the nearby users may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 13:
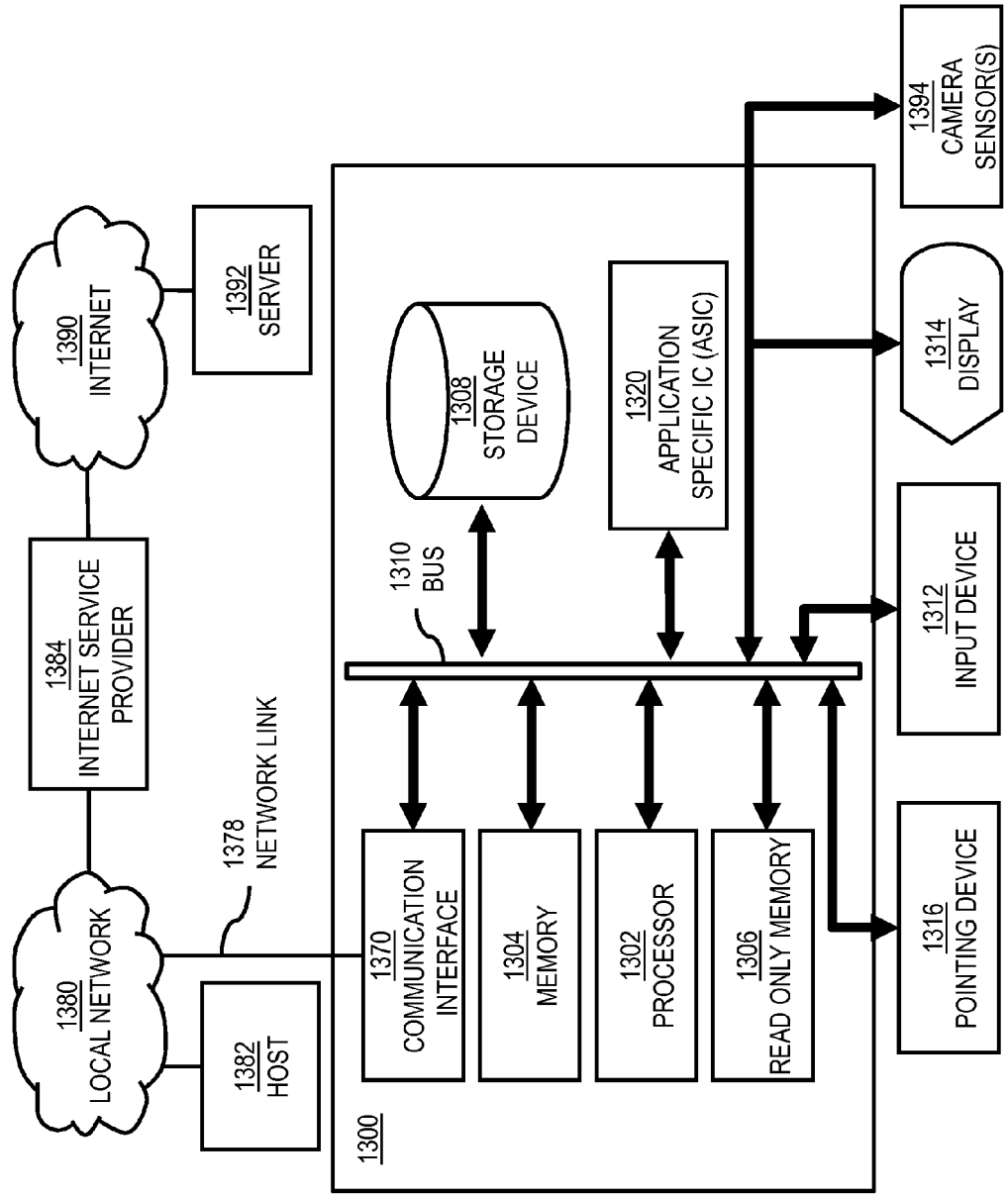
FIG. 13 is a diagram of hardware that can be used to implement an embodiment of the invention.

FIG. 13 illustrates a computer system 1300 upon which an embodiment of the invention may be implemented. Although computer system 1300 is depicted with respect to a particular device or equipment, it is contemplated that other devices or equipment (e.g., network elements, servers, etc.) within FIG. 13 can deploy the illustrated hardware and components of system 1300. Computer system 1300 is programmed (e.g., via computer program code or instructions) to provide alarm notification to the intended user while minimizing disturbance to the nearby users as described herein and includes a communication mechanism such as a bus 1310 for passing information between other internal and external components of the computer system 1300. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of providing alarm notification to the intended user while minimizing disturbance to the nearby users.

A bus 1310 includes one or more parallel conductors of information so that information is transferred quickly among devices coupled to the bus 1310. One or more processors 1302 for processing information are coupled with the bus 1310.

A processor (or multiple processors) 1302 performs a set of operations on information as specified by computer program code related to providing alarm notification to the intended user while minimizing disturbance to the nearby users. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1310 and placing information on the bus 1310. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1302, such as a sequence of operation codes, constitute processor instructions, also called computer system instructions or, simply, computer instructions. Processors may be implemented as mechanical, electrical, magnetic, optical, chemical, or quantum components, among others, alone or in combination.

Computer system 1300 also includes a memory 1304 coupled to bus 1310. The memory 1304, such as a random access memory (RAM) or any other dynamic storage device, stores information including processor instructions for providing alarm notification to the intended user while minimizing disturbance to the nearby users. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of processor instructions. The computer system 1300 also includes a read only memory (ROM) 1306 or any other static storage device coupled to the bus 1310 for storing static information, including instructions, that is not changed by the computer system 1300. Some memory is composed of volatile storage that loses the information stored thereon when power is lost. Also coupled to bus 1310 is a non-volatile (persistent) storage device 1308, such as a magnetic disk, optical disk or flash card, for storing information, including instructions, that persists even when the computer system 1300 is turned off or otherwise loses power.

Information, including instructions for providing alarm notification to the intended user while minimizing disturbance to the nearby users, is provided to the bus 1310 for use by the processor from an external input device 1312, such as a keyboard containing alphanumeric keys operated by a human user, a microphone, an Infrared (IR) remote control, a joystick, a game pad, a stylus pen, a touch screen, or a sensor. A sensor detects conditions in its vicinity and transforms those detections into physical expression compatible with the measurable phenomenon used to represent information in computer system 1300. Other external devices coupled to bus 1310, used primarily for interacting with humans, include a display device 1314, such as a cathode ray tube (CRT), a liquid crystal display (LCD), a light emitting diode (LED) display, an organic LED (OLED) display, a plasma screen, or a printer for presenting text or images, and a pointing device 1316, such as a mouse, a trackball, cursor direction keys, or a motion sensor, for controlling a position of a small cursor image presented on the display 1314 and issuing commands associated with graphical elements presented on the display 1314, and one or more camera sensors 1394 for capturing, recording and causing to store one or more still and/or moving images (e.g., videos, movies, etc.) which also may comprise audio recordings. In some embodiments, for example, in embodiments in which the computer system 1300 performs all functions automatically without human input, one or more of external input device 1312, display device 1314 and pointing device 1316 may be omitted.

In the illustrated embodiment, special purpose hardware, such as an application specific integrated circuit (ASIC) 1320, is coupled to bus 1310. The special purpose hardware is configured to perform operations not performed by processor 1302 quickly enough for special purposes. Examples of ASICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a one-way or two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer.

In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. For wireless links, the communications interface 1370 sends or receives or both sends and receives electrical, acoustic or electromagnetic signals, including infrared and optical signals, that carry information streams, such as digital data. For example, in wireless handheld devices, such as mobile telephones like cell phones, the communications interface 1370 includes a radio band electromagnetic transmitter and receiver called a radio transceiver. In certain embodiments, the communications interface 1370 enables connection to the communication network 107 for providing alarm notification to the intended user while minimizing disturbance to the nearby users to the UE 101.

The term "computer-readable medium" as used herein refers to any medium that participates in providing information to processor 1302, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 1308. Volatile media include, for example, dynamic memory 1304. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1320.

Network link 1378 typically provides information communication using transmission media through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390.

A computer called a server host 1392 connected to the Internet hosts a process that provides a service in response to information received over the Internet. For example, server host 1392 hosts a process that provides information representing video data for presentation at display 1314. It is contemplated that the components of system 1300 can be deployed in various configurations within other computer systems, e.g., host 1382 and server 1392.

At least some embodiments of the invention are related to the use of computer system 1300 for implementing some or all of the techniques described herein. According to one embodiment of the invention, those techniques are performed by computer system 1300 in response to processor 1302 executing one or more sequences of one or more processor instructions contained in memory 1304. Such instructions, also called computer instructions, software and program code, may be read into memory 1304 from another computer-readable medium such as storage device 1308 or network link 1378. Execution of the sequences of instructions contained in memory 1304 causes processor 1302 to perform one or more of the method steps described herein. In alternative embodiments, hardware, such as ASIC 1320, may be used in place of or in combination with software to implement the invention. Thus, embodiments of the invention are not limited to any specific combination of hardware and software, unless otherwise explicitly stated herein.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server host 1392 transmits program code for a particular application, requested by a message sent from computer 1300, through Internet 1390, ISP equipment 1384, local network 1380 and communications interface 1370. The received code may be executed by processor 1302 as it is received, or may be stored in memory 1304 or in storage device 1308 or any other non-volatile storage for later execution, or both. In this manner, computer system 1300 may obtain application program code in the form of signals on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

FIG. 14 illustrates a chip set or chip 1400 upon which an embodiment of the invention may be implemented. Chip set 1400 is programmed to provide alarm notification to the intended user while minimizing disturbance to the nearby users as described herein and includes, for instance, the processor and memory components described with respect to FIG. 13 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 1400 can be implemented in a single chip. It is further contemplated that in certain embodiments the chip set or chip 1400 can be implemented as a single "system on a chip." It is further contemplated that in certain embodiments a separate ASIC would not be used, for example, and that all relevant functions as disclosed herein would be performed by a processor or processors. Chip set or chip 1400, or a portion thereof, constitutes a means for performing one or more steps of providing user interface navigation information associated with the availability of functions. Chip set or chip 1400, or a portion thereof, constitutes a means for performing one or more steps of providing alarm notification to the intended user while minimizing disturbance to the nearby users.

In one embodiment, the chip set or chip 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a more general purpose processor. Other specialized components to aid in performing the inventive functions described herein may include one or more field programmable gate arrays (FPGA), one or more controllers, or one or more other special-purpose computer chips.

In one embodiment, the chip set or chip 1400 includes merely one or more processors and some software and/or firmware supporting and/or relating to and/or for the one or more processors.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform the inventive steps described herein to provide alarm notification to the intended user while minimizing disturbance to the nearby users. The memory 1405 also stores the data associated with or generated by the execution of the inventive steps.

Figure 15:
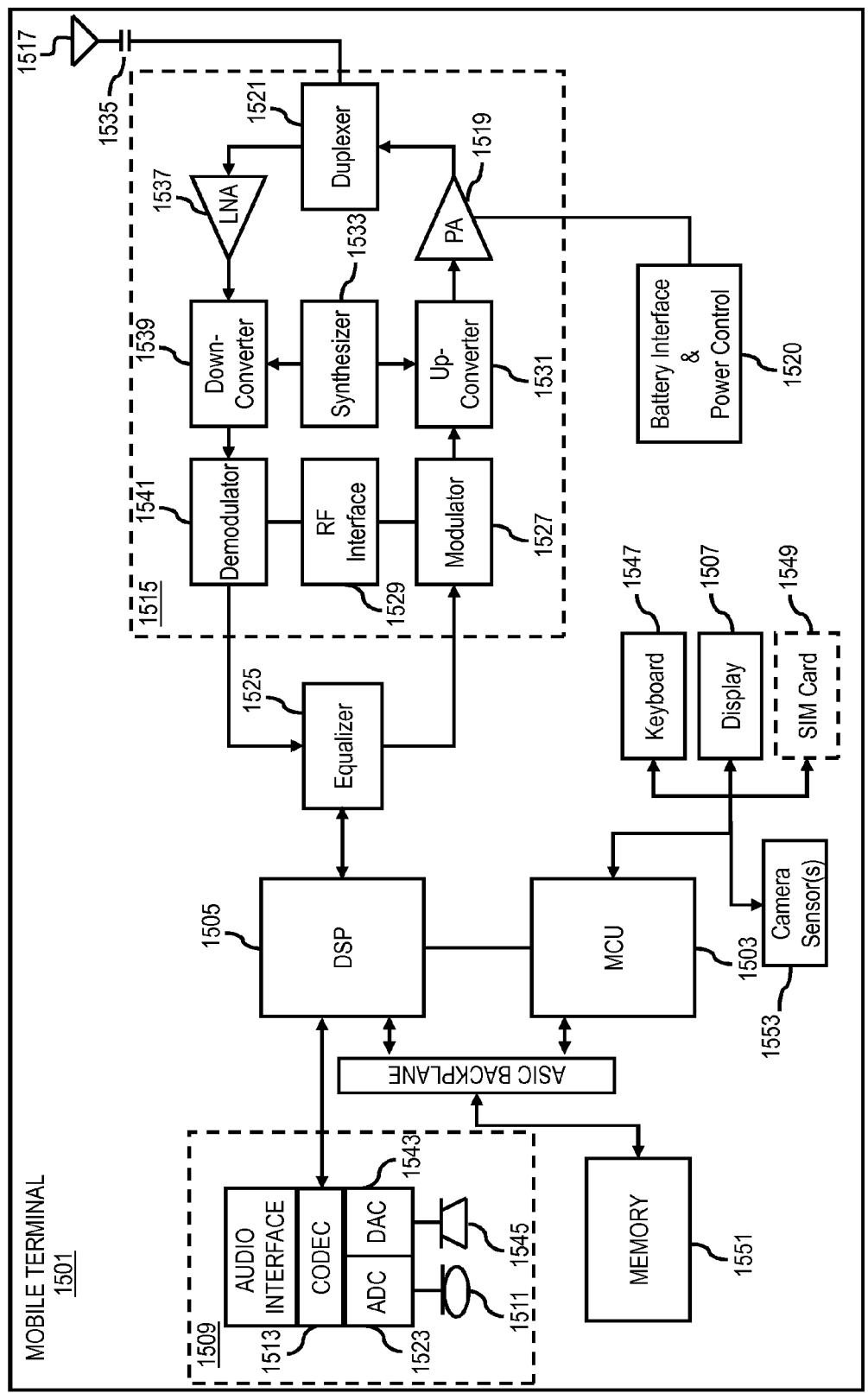
FIG. 15 is a diagram of a mobile terminal (e.g., handset) that can be used to implement an embodiment of the invention.

FIG. 15 is a diagram of exemplary components of a mobile terminal (e.g., handset) for communications, which is capable of operating in the system of FIG. 1, according to one embodiment. In some embodiments, mobile terminal 1501, or a portion thereof, constitutes a means for performing one or more steps of providing alarm notification to the intended user while minimizing disturbance to the nearby users. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1503, a Digital Signal Processor (DSP) 1505, and a receiver/transmitter unit including a microphone gain control unit and a speaker gain control unit. A main display unit 1507 provides a display to the user in support of various applications and mobile terminal functions that perform or support the steps of providing alarm notification to the intended user while minimizing disturbance to the nearby users. The display 1507 includes display circuitry configured to display at least a portion of a user interface of the mobile terminal (e.g., mobile telephone). Additionally, the display 1507 and display circuitry are configured to facilitate user control of at least some functions of the mobile terminal. An audio function circuitry 1509 includes a microphone 1511 and microphone amplifier that amplifies the speech signal output from the microphone 1511. The amplified speech signal output from the microphone 1511 is fed to a coder/decoder (CODEC) 1513.

A radio section 1515 amplifies power and converts frequency in order to communicate with a base station, which is included in a mobile communication system, via antenna 1517. The power amplifier (PA) 1519 and the transmitter/modulation circuitry are operationally responsive to the MCU 1503, with an output from the PA 1519 coupled to the duplexer 1521 or circulator or antenna switch, as known in the art. The PA 1519 also couples to a battery interface and power control unit 1520.

In use, a user of mobile terminal 1501 speaks into the microphone 1511 and his or her voice along with any detected background noise is converted into an analog voltage. The analog voltage is then converted into a digital signal through the Analog to Digital Converter (ADC) 1523. The control unit 1503 routes the digital signal into the DSP 1505 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1525 for compensation of any frequency-dependent impairments that occur during transmission though the air such as phase and amplitude distortion. After equalizing the bit stream, the modulator 1527 combines the signal with a RF signal generated in the RF interface 1529. The modulator 1527 generates a sine wave by way of frequency or phase modulation. In order to prepare the signal for transmission, an up-converter 1531 combines the sine wave output from the modulator 1527 with another sine wave generated by a synthesizer 1533 to achieve the desired frequency of transmission. The signal is then sent through a PA 1519 to increase the signal to an appropriate power level. In practical systems, the PA 1519 acts as a variable gain amplifier whose gain is controlled by the DSP 1505 from information received from a network base station. The signal is then filtered within the duplexer 1521 and optionally sent to an antenna coupler 1535 to match impedances to provide maximum power transfer. Finally, the signal is transmitted via antenna 1517 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1501 are received via antenna 1517 and immediately amplified by a low noise amplifier (LNA) 1537. A down-converter 1539 lowers the carrier frequency while the demodulator 1541 strips away the RF leaving only a digital bit stream. The signal then goes through the equalizer 1525 and is processed by the DSP 1505. A Digital to Analog Converter (DAC) 1543 converts the signal and the resulting output is transmitted to the user through the speaker 1545, all under control of a Main Control Unit (MCU) 1503 which can be implemented as a Central Processing Unit (CPU).

The MCU 1503 receives various signals including input signals from the keyboard 1547. The keyboard 1547 and/or the MCU 1503 in combination with other user input components (e.g., the microphone 1511) comprise a user interface circuitry for managing user input. The MCU 1503 runs a user interface software to facilitate user control of at least some functions of the mobile terminal 1501 to provide alarm notification to the intended user while minimizing disturbance to the nearby users. The MCU 1503 also delivers a display command and a switch command to the display 1507 and to the speech output switching controller, respectively. Further, the MCU 1503 exchanges information with the DSP 1505 and can access an optionally incorporated SIM card 1549 and a memory 1551. In addition, the MCU 1503 executes various control functions required of the terminal. The DSP 1505 may, depending upon the implementation, perform any of a variety of conventional digital processing functions on the voice signals. Additionally, DSP 1505 determines the background noise level of the local environment from the signals detected by microphone 1511 and sets the gain of microphone 1511 to a level selected to compensate for the natural tendency of the user of the mobile terminal 1501.

The CODEC 1513 includes the ADC 1523 and DAC 1543. The memory 1551 stores various data including call incoming tone data and is capable of storing other data including music data received via, e.g., the global Internet. The software module could reside in RAM memory, flash memory, registers, or any other form of writable storage medium known in the art. The memory device 1551 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1549 carries, for instance, important information, such as the cellular phone number, the carrier supplying service, subscription details, and security information. The SIM card 1549 serves primarily to identify the mobile terminal 1501 on a radio network. The card 1549 also contains a memory for storing a personal telephone number registry, text messages, and user specific mobile terminal settings.

Further, one or more camera sensors 1553 may be incorporated onto the mobile station 1501 wherein the one or more camera sensors may be placed at one or more locations on the mobile station. Generally, the camera sensors may be utilized to capture, record, and cause to store one or more still and/or moving images (e.g., videos, movies, etc.) which also may comprise audio recordings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising:
   processing, via a processor, of sensor information collected while at least one first user and at least one second user are asleep to determine at least one first breathing rhythm associated with at least one first user, at least one second breathing rhythm associated with at least one second user, or a combination thereof; and
   determining one or more alarm notification parameters to cause, at least in part, an adjustment of at least one sound rhythm of the one or more alarm notifications to match the at least one second breathing rhythm for the alarm notifications directed to the at least one first user.

2. A method of claim 1, further comprising:
   processing of the sensor information to determine at least one first sleeping pattern associated with the at least one first user, at least one second sleeping pattern associated with the at least one second user, or a combination thereof during a specified time period; and
   determining one or more alarm notification parameter to cause, at last in part, an adjustment of timing of the one or more alarm notification to match the at least one second sleeping pattern for the alarm notifications directed to the at least one first user.

3. A method of claim 1, further comprising:
   causing, at least in part, a synchronization of the sensor information associated with the at least one first user, the at least one second user, or a combination thereof, wherein the synchronization of the sensor information includes removing any undesired sounds; and causing, at least in part, a comparison of the synchronized sensor information to determine the one or more alarm notification parameters for the one or more alarm notifications.

4. A method of claim 1, further comprising:

determining a difference between the at least one first breathing rhythm associated with the at least one first user, the at least one second breathing rhythm associated with the at least one second user, or a combination thereof; and causing, at least in part, the one or more alarm notifications based, at least in part, on the difference.

5. A method of claim 1, further comprising:

causing, at least in part, an implementation of directional sound analysis to detect the direction of the at least one first user, the at least one second user, or a combination thereof; and causing, at least in part, a channeling of the one or more alarm notifications towards the direction of the at least one first user, the at least one second user, or a combination thereof.

6. A method of claim 1, further comprising:

causing, at least in part, a detection of direction for the at least one first user, the at least one second user, or a combination thereof based, at least in part, on one or more voice commands; and causing, at least in part, a channeling of the one or more alarm notifications in the directions of the voice command of the at least one first user, the at least one second user, or a combination thereof.

7. A method of claim 1, further comprising:

causing, at least in part, a separation of the breathing rhythm for the at least one first user, the at least one second user, or a combination thereof; and causing, at least in part, a monitoring of the separated breathing rhythm for the at least one first user, the at least one second user, or a combination thereof in real-time, periodically, according to schedule, on demand, or a combination thereof.

8. A method of claim 2, wherein the at least one first sleeping pattern, the at least one second sleeping pattern, or a combination thereof include, at least in part, a status of sleep, a status of snoring, a sleeping position, or a combination thereof.

9. An apparatus comprising:

at least one processor; and at least one memory including computer program code for one or more programs, the at least one memory and the computer program code configured to, with the at least one processor, cause the apparatus to perform at least the following, process, via a processor, of the sensor information collected while at least one first user and at least one second user are asleep to determine at least one first breathing rhythm associated with at least one first user, at least one second breathing rhythm associated with at least one second user, or a combination thereof and sleep characteristic information for the at least one first user, the at least one second user, or a combination thereof; and determine one or more alarm notification parameters to cause, at least in part, an adjustment of at least one sound rhythm of the one or more alarm notifications to match the at least one second breathing rhythm for the alarm notifications directed to the at least one first user.

10. An apparatus of claim 9, wherein the apparatus is further caused to:

process the sensor information to determine at least one first sleeping pattern associated with the at least one first user, at least one second sleeping pattern associated with the at least one second user, or a combination thereof during a specified time period; and determine one or more alarm notification parameter to cause, at last in part, an adjustment of timing of the one or more alarm notification to match the at least one second sleeping pattern for the alarm notifications directed to the at least one first user.

11. An apparatus of claim 9, wherein the apparatus is further caused to:

cause, at least in part, a synchronization of the sensor information associated with the at least one first user, the at least one second user, or a combination thereof, wherein the synchronization of the sensor information includes removing any undesired sound; and cause, at least in part, a comparison of the synchronized sensor information to determine the one or more alarm notification parameters for the one or more alarm notifications.

12. An apparatus of claim 9, wherein the apparatus is further caused to:

determine a difference between the at least one first breathing rhythm associated with the at least one first user, the at least one second breathing rhythm associated with the at least one second user, or a combination thereof and cause, at least in part, the one or more alarm notifications based, at least in part, on the difference.

13. An apparatus of claim 9, wherein the apparatus is further caused to:

cause, at least in part, an implementation of directional sound analysis to detect the direction of the at least one first user, the at least one second user, or a combination thereof; and cause, at least in part, a channeling of the one or more alarm notifications towards the direction of the at least one first user, the at least one second user, or a combination thereof.

14. A non-transitory computer-readable storage medium carrying one or more sequences of one or more instructions which, when executed by one or more processors, cause an apparatus to at least perform the following steps:

process, via a processor, of the sensor information collected while at least one first user and at least one second user are asleep to determine at least one first breathing rhythm associated with at least one first user, at least one second breathing rhythm associated with at least one second user, or a combination thereof; and determine one or more alarm notification parameters to cause, at least in part, an adjustment of at least one sound rhythm of the one or more alarm notifications to match the at least one second breathing rhythm for the alarm notifications directed to the at least one first user.

15. A method of claim 1, wherein the alarm notification parameters includes a direction for the alarm notification, a pattern for the alarm notification, a duration for the alarm notification, a level for the alarm notification, or a combination thereof.

16. A method of claim 2, further comprising:
causing, at least in part, a visualization of the at least one first sleeping pattern, the at least one second sleeping pattern, or a combination thereof,
wherein visualization includes graphical representation of a status of sleep for the at least one first user, the at least one second user, or a combination thereof.

17. An apparatus of claim 9, wherein the alarm notification parameters includes a direction for the alarm notification, a pattern for the alarm notification, a duration for the alarm notification, a level of alarm notification, or a combination thereof.

18. An apparatus of claim 10, wherein the at least one first sleeping pattern, the at least one second sleeping pattern, or a combination thereof include, at least in part, a status of sleep, a status of snoring, a sleeping position, or a combination thereof.

19. A non-transitory computer-readable storage medium of claim 14, wherein the apparatus is further caused to:
process the sensor information to determine at least one first sleeping pattern associated with the at least one first user, at least one second sleeping pattern associated with the at least one second user, or a combination thereof during a specified time period; and
determine one or more alarm notification parameter to cause, at last in part, an adjustment of timing of the one or more alarm notification to match the at least one second sleeping pattern for the alarm notifications directed to the at least one first user.

20. A non-transitory computer-readable storage medium of claim 14, wherein the alarm notification parameters includes a direction for the alarm notification, a pattern for the alarm notification, a duration for the alarm notification, a level of alarm notification, or a combination thereof.

* * * * *